(12) United States Patent
Lutter et al.

(10) Patent No.: US 11,213,387 B2
(45) Date of Patent: *Jan. 4, 2022

(54) TRUNCATED CONE HEART VALVE STENT

(71) Applicants: Georg Lutter, Kiel (DE); Lucian Lozonschi, Madison, WI (US)

(72) Inventors: Georg Lutter, Kiel (DE); Lucian Lozonschi, Madison, WI (US)

(*) Notice: Subject to any disclaimer, the term of this patent is extended or adjusted under 35 U.S.C. 154(b) by 17 days.

This patent is subject to a terminal disclaimer.

(21) Appl. No.: 16/565,564

(22) Filed: Sep. 10, 2019

(65) Prior Publication Data

US 2020/0000583 A1 Jan. 2, 2020

Related U.S. Application Data

(60) Continuation of application No. 15/653,653, filed on Jul. 19, 2017, now Pat. No. 10,456,248, which is a
(Continued)

(30) Foreign Application Priority Data

Sep. 13, 2007 (DE) .......................... 102007043830.5

(51) Int. Cl.
*A61F 2/24* (2006.01)
*A61B 17/04* (2006.01)
*A61B 17/00* (2006.01)

(52) U.S. Cl.
CPC ........ *A61F 2/2418* (2013.01); *A61B 17/0401* (2013.01); *A61F 2/2445* (2013.01); *A61F 2/2457* (2013.01); *A61F 2/2487* (2013.01); *A61B 2017/00243* (2013.01); *A61B 2017/0496* (2013.01); *A61F 2/2436* (2013.01); *A61F 2220/0008* (2013.01); *A61F 2230/005* (2013.01); *A61F 2230/0008* (2013.01); *A61F 2230/0013* (2013.01);
(Continued)

(58) Field of Classification Search
CPC .......... A61F 2/24; A61F 2/2418; A61B 17/04; A61B 17/0401
See application file for complete search history.

(56) References Cited

U.S. PATENT DOCUMENTS 2,697,008 A 12/1954 Ross
3,409,013 A 11/1968 Berry
(Continued)

FOREIGN PATENT DOCUMENTS

CN 1486161 A 3/2004
CN 1961845 A 5/2007
(Continued)

OTHER PUBLICATIONS

US 9,155,620 B2, 10/2015, Gross et al. (withdrawn)
(Continued)

*Primary Examiner* — Matthew W Schall
(74) *Attorney, Agent, or Firm* — Lerner, David, Littenberg, Krumholz & mentlik, LLP

(57) ABSTRACT

A heart valve stent having a section with a heart valve implant and several proximally disposed tissue anchors, also comprising a plurality of anchoring threats, each with a proximate end fastened to the stent or valve and a distal end attached to tissue within a heart chamber to provide tension between the heart chamber tissue and the stent.

18 Claims, 11 Drawing Sheets

Related U.S. Application Data continuation of application No. 15/018,473, filed on Feb. 8, 2016, now Pat. No. 9,730,792, which is a continuation of application No. 14/746,381, filed on Jun. 22, 2015, now Pat. No. 9,254,192, which is a division of application No. 14/465,437, filed on Aug. 21, 2014, now Pat. No. 9,078,749, which is a continuation of application No. 13/275,683, filed on Oct. 18, 2011, now Pat. No. 9,095,433, which is a continuation of application No. 12/677,958, filed as application No. PCT/DE2008/001515 on Sep. 10, 2008, now abandoned.

(52) U.S. Cl.
CPC .............. *A61F 2230/0054* (2013.01); *A61F 2230/0067* (2013.01); *A61F 2230/0069* (2013.01); *A61F 2230/0078* (2013.01); *A61F 2250/001* (2013.01)

(56) References Cited

U.S. PATENT DOCUMENTS

| | | |
|---|---|---|
| 3,472,230 A | 10/1969 | Fogarty et al. |
| 3,476,101 A | 11/1969 | Ross |
| 3,548,417 A | 12/1970 | Kischer |
| 3,587,115 A | 6/1971 | Shiley |
| 3,657,744 A | 4/1972 | Ersek |
| 3,671,979 A | 6/1972 | Moulopoulos |
| 3,714,671 A | 2/1973 | Edwards et al. |
| 3,755,823 A | 9/1973 | Hancock |
| 3,976,079 A | 8/1976 | Samuels et al. |
| 4,003,382 A | 1/1977 | Dyke |
| 4,035,849 A | 7/1977 | Angell et al. |
| 4,056,854 A | 11/1977 | Boretos et al. |
| 4,073,438 A | 2/1978 | Meyer |
| 4,106,129 A | 8/1978 | Carpentier et al. |
| 4,222,126 A | 9/1980 | Boretos et al. |
| 4,265,694 A | 5/1981 | Boretos et al. |
| 4,297,749 A | 11/1981 | Davis et al. |
| 4,339,831 A | 7/1982 | Johnson |
| 4,343,048 A | 8/1982 | Ross et al. |
| 4,345,340 A | 8/1982 | Rosen |
| 4,373,216 A | 2/1983 | Klawitter |
| 4,406,022 A | 9/1983 | Roy |
| 4,470,157 A | 9/1984 | Love |
| 4,490,859 A | 1/1985 | Black et al. |
| 4,535,483 A | 8/1985 | Klawitter et al. |
| 4,574,803 A | 3/1986 | Storz |
| 4,585,705 A | 4/1986 | Broderick et al. |
| 4,592,340 A | 6/1986 | Boyles |
| 4,605,407 A | 8/1986 | Black et al. |
| 4,612,011 A | 9/1986 | Kautzky |
| 4,626,255 A | 12/1986 | Reichart et al. |
| 4,638,886 A | 1/1987 | Marietta |
| 4,643,732 A | 2/1987 | Pietsch et al. |
| 4,655,771 A | 4/1987 | Wallsten |
| 4,692,164 A | 9/1987 | Dzemeshkevich et al. |
| 4,733,665 A | 3/1988 | Palmaz |
| 4,759,758 A | 7/1988 | Gabbay |
| 4,762,128 A | 8/1988 | Rosenbluth |
| 4,777,951 A | 10/1988 | Cribier et al. |
| 4,787,899 A | 11/1988 | Lazarus |
| 4,787,901 A | 11/1988 | Baykut |
| 4,796,629 A | 1/1989 | Grayzel |
| 4,824,180 A | 4/1989 | Levrai |
| 4,829,990 A | 5/1989 | Thuroff et al. |
| 4,830,117 A | 5/1989 | Capasso |
| 4,851,001 A | 7/1989 | Taheri |
| 4,856,516 A | 8/1989 | Hillstead |
| 4,878,495 A | 11/1989 | Grayzel |
| 4,878,906 A | 11/1989 | Lindemann et al. |
| 4,883,458 A | 11/1989 | Shiber |
| 4,922,905 A | 5/1990 | Strecker |
| 4,923,013 A | 5/1990 | Gennaro |
| 4,960,424 A | 10/1990 | Grooters |
| 4,966,604 A | 10/1990 | Reiss |
| 4,979,939 A | 12/1990 | Shiber |
| 4,986,830 A | 1/1991 | Owens et al. |
| 4,994,077 A | 2/1991 | Dobben |
| 4,996,873 A | 3/1991 | Takeuchi |
| 5,007,896 A | 4/1991 | Shiber |
| 5,026,366 A | 6/1991 | Leckrone |
| 5,032,128 A | 7/1991 | Alonso |
| 5,035,706 A | 7/1991 | Giantureo et al. |
| 5,037,434 A | 8/1991 | Lane |
| 5,047,041 A | 9/1991 | Samuels |
| 5,059,177 A | 10/1991 | Towne et al. |
| 5,064,435 A | 11/1991 | Porter |
| 5,080,668 A | 1/1992 | Bolz et al. |
| 5,085,635 A | 2/1992 | Cragg |
| 5,089,015 A | 2/1992 | Ross |
| 5,152,771 A | 10/1992 | Sabbaghian et al. |
| 5,163,953 A | 11/1992 | Vince |
| 5,167,628 A | 12/1992 | Boyles |
| 5,192,297 A | 3/1993 | Hull |
| 5,201,880 A | 4/1993 | Wright et al. |
| 5,266,073 A | 11/1993 | Wall |
| 5,282,847 A | 2/1994 | Trescony et al. |
| 5,295,958 A | 3/1994 | Shturman |
| 5,306,296 A | 4/1994 | Wright et al. |
| 5,332,402 A | 7/1994 | Teitelbaum |
| 5,336,616 A | 8/1994 | Livesey et al. |
| 5,344,442 A | 9/1994 | Deac |
| 5,360,444 A | 11/1994 | Kusuhara |
| 5,364,407 A | 11/1994 | Poll |
| 5,370,685 A | 12/1994 | Stevens |
| 5,397,351 A | 3/1995 | Pavcnik et al. |
| 5,411,055 A | 5/1995 | Kane |
| 5,411,552 A | 5/1995 | Andersen et al. |
| 5,415,667 A | 5/1995 | Frater |
| 5,443,446 A | 8/1995 | Shturman |
| 5,480,424 A | 1/1996 | Cox |
| 5,500,014 A | 3/1996 | Quijano et al. |
| 5,545,209 A | 8/1996 | Roberts et al. |
| 5,545,214 A | 8/1996 | Stevens |
| 5,549,665 A | 8/1996 | Vesely et al. |
| 5,554,184 A | 9/1996 | Machiraju |
| 5,554,185 A | 9/1996 | Block et al. |
| 5,571,175 A | 11/1996 | Vanney et al. |
| 5,591,185 A | 1/1997 | Kilmer et al. |
| 5,607,462 A | 3/1997 | Imran |
| 5,607,464 A | 3/1997 | Trescony et al. |
| 5,609,626 A | 3/1997 | Quijano et al. |
| 5,639,274 A | 6/1997 | Fischell et al. |
| 5,662,704 A | 9/1997 | Gross |
| 5,665,115 A | 9/1997 | Cragg |
| 5,674,279 A | 10/1997 | Wright et al. |
| 5,697,905 A | 12/1997 | d'Ambrosio |
| 5,702,368 A | 12/1997 | Stevens et al. |
| 5,716,417 A | 2/1998 | Girard et al. |
| 5,728,068 A | 3/1998 | Leone et al. |
| 5,728,151 A | 3/1998 | Garrison et al. |
| 5,735,842 A | 4/1998 | Krueger et al. |
| 5,741,333 A | 4/1998 | Frid |
| 5,749,890 A | 5/1998 | Shaknovich |
| 5,756,476 A | 5/1998 | Epstein et al. |
| 5,769,812 A | 6/1998 | Stevens et al. |
| 5,792,179 A | 8/1998 | Sideris |
| 5,800,508 A | 9/1998 | Goicoechea et al. |
| 5,833,673 A | 11/1998 | Ockuly et al. |
| 5,840,081 A | 11/1998 | Andersen et al. |
| 5,855,597 A | 1/1999 | Jayaraman |
| 5,855,601 A | 1/1999 | Bessler et al. |
| 5,855,602 A | 1/1999 | Angell |
| 5,904,697 A | 5/1999 | Gifford, III et al. |
| 5,925,063 A | 7/1999 | Khosravi |
| 5,957,949 A | 9/1999 | Leonhardt et al. |
| 5,968,052 A | 10/1999 | Sullivan, III et al. |
| 5,968,068 A | 10/1999 | Dehdashtian et al. |
| 5,972,030 A | 10/1999 | Garrison et al. |
| 5,993,481 A | 11/1999 | Marcade et al. |
| 6,027,525 A | 2/2000 | Suh et al. |

(56) References Cited

U.S. PATENT DOCUMENTS

| | | |
|---|---|---|
| 6,042,607 A | 3/2000 | Williamson, IV et al. |
| 6,045,497 A | 4/2000 | Schweich, Jr. et al. |
| 6,063,112 A | 5/2000 | Sgro |
| 6,077,214 A | 6/2000 | Mortier et al. |
| 6,099,508 A | 8/2000 | Bousquet |
| 6,132,473 A | 10/2000 | Williams et al. |
| 6,168,614 B1 | 1/2001 | Andersen et al. |
| 6,171,335 B1 | 1/2001 | Wheatley et al. |
| 6,174,327 B1 | 1/2001 | Mertens et al. |
| 6,183,411 B1 | 2/2001 | Mortier et al. |
| 6,210,408 B1 | 4/2001 | Chandrasekaran et al. |
| 6,217,585 B1 | 4/2001 | Houser et al. |
| 6,221,091 B1 | 4/2001 | Khosravi |
| 6,231,602 B1 | 5/2001 | Carpentier et al. |
| 6,245,102 B1 | 6/2001 | Jayaraman |
| 6,260,552 B1 | 7/2001 | Mortier et al. |
| 6,261,222 B1 | 7/2001 | Schweich, Jr. et al. |
| 6,264,602 B1 | 7/2001 | Mortier et al. |
| 6,287,339 B1 | 9/2001 | Vazquez et al. |
| 6,299,637 B1 | 10/2001 | Shaolian et al. |
| 6,302,906 B1 | 10/2001 | Goicoechea et al. |
| 6,312,465 B1 | 11/2001 | Griffin et al. |
| 6,332,893 B1 | 12/2001 | Mortier et al. |
| 6,350,277 B1 | 2/2002 | Kocur |
| 6,358,277 B1 | 3/2002 | Duran |
| 6,379,372 B1 | 4/2002 | Dehdashtian et al. |
| 6,402,679 B1 | 6/2002 | Mortier et al. |
| 6,402,680 B2 | 6/2002 | Mortier et al. |
| 6,402,781 B1 | 6/2002 | Langberg et al. |
| 6,406,420 B1 | 6/2002 | McCarthy et al. |
| 6,425,916 B1 | 7/2002 | Garrison et al. |
| 6,440,164 B1 | 8/2002 | DiMatteo et al. |
| 6,454,799 B1 | 9/2002 | Schreck |
| 6,458,153 B1 | 10/2002 | Bailey et al. |
| 6,461,382 B1 | 10/2002 | Cao |
| 6,468,660 B2 | 10/2002 | Ogle et al. |
| 6,482,228 B1 | 11/2002 | Norred |
| 6,488,704 B1 | 12/2002 | Connelly et al. |
| 6,537,198 B1 | 3/2003 | Vidlund et al. |
| 6,540,782 B1 | 4/2003 | Snyders |
| 6,569,196 B1 | 5/2003 | Vesely |
| 6,575,252 B2 | 6/2003 | Reed |
| 6,582,462 B1 | 6/2003 | Andersen et al. |
| 6,605,112 B1 | 8/2003 | Moll et al. |
| 6,616,684 B1 | 9/2003 | Vidlund et al. |
| 6,622,730 B2 | 9/2003 | Ekvall et al. |
| 6,629,534 B1 | 10/2003 | St. Goar et al. |
| 6,629,921 B1 | 10/2003 | Schweich, Jr. et al. |
| 6,648,077 B2 | 11/2003 | Hoffman |
| 6,648,921 B2 | 11/2003 | Anderson et al. |
| 6,652,578 B2 | 11/2003 | Bailey et al. |
| 6,669,724 B2 | 12/2003 | Park et al. |
| 6,706,065 B2 | 3/2004 | Langberg et al. |
| 6,709,456 B2 | 3/2004 | Langberg et al. |
| 6,723,038 B1 | 4/2004 | Schroeder et al. |
| 6,726,715 B2 | 4/2004 | Sutherland |
| 6,730,118 B2 | 5/2004 | Spenser et al. |
| 6,733,525 B2 | 5/2004 | Yang et al. |
| 6,740,105 B2 | 5/2004 | Yodfat et al. |
| 6,746,401 B2 | 6/2004 | Panescu |
| 6,746,471 B2 | 6/2004 | Mortier et al. |
| 6,752,813 B2 | 6/2004 | Goldfarb et al. |
| 6,764,510 B2 | 7/2004 | Vidlund et al. |
| 6,797,002 B2 | 9/2004 | Spence et al. |
| 6,810,882 B2 | 11/2004 | Langberg et al. |
| 6,830,584 B1 | 12/2004 | Seguin |
| 6,854,668 B2 | 2/2005 | Wancho et al. |
| 6,855,144 B2 | 2/2005 | Lesh |
| 6,858,001 B1 | 2/2005 | Aboul-Hosn |
| 6,890,353 B2 | 5/2005 | Cohn et al. |
| 6,893,460 B2 | 5/2005 | Spenser et al. |
| 6,896,690 B1 | 5/2005 | Lambrecht et al. |
| 6,908,424 B2 | 6/2005 | Mortier et al. |
| 6,908,481 B2 | 6/2005 | Cribier |
| 6,936,067 B2 | 8/2005 | Buchanan |
| 6,945,996 B2 | 9/2005 | Sedransk |
| 6,955,175 B2 | 10/2005 | Stevens et al. |
| 6,974,476 B2 | 12/2005 | McGuckin, Jr. et al. |
| 6,976,543 B1 | 12/2005 | Fischer |
| 6,997,950 B2 | 2/2006 | Chawla |
| 7,018,406 B2 | 3/2006 | Seguin et al. |
| 7,018,408 B2 | 3/2006 | Bailey et al. |
| 7,044,905 B2 | 5/2006 | Vidlund et al. |
| 7,060,021 B1 | 6/2006 | Wilk |
| 7,077,862 B2 | 7/2006 | Vidlund et al. |
| 7,087,064 B1 | 8/2006 | Hyde |
| 7,100,614 B2 | 9/2006 | Stevens et al. |
| 7,101,395 B2 | 9/2006 | Tremulis et al. |
| 7,108,717 B2 | 9/2006 | Freidberg |
| 7,112,219 B2 | 9/2006 | Vidlund et al. |
| 7,115,141 B2 | 10/2006 | Menz et al. |
| 7,141,064 B2 | 11/2006 | Scott et al. |
| 7,175,656 B2 | 2/2007 | Khairkhahan |
| 7,198,646 B2 | 4/2007 | Figulla et al. |
| 7,201,772 B2 | 4/2007 | Schwammenthal et al. |
| 7,247,134 B2 | 7/2007 | Vidlund et al. |
| 7,252,682 B2 | 8/2007 | Seguin |
| 7,267,686 B2 | 9/2007 | DiMatteo et al. |
| 7,275,604 B1 | 10/2007 | Wall |
| 7,276,078 B2 | 10/2007 | Spenser et al. |
| 7,276,084 B2 | 10/2007 | Yang et al. |
| 7,316,706 B2 | 1/2008 | Bloom et al. |
| 7,318,278 B2 | 1/2008 | Zhang et al. |
| 7,326,236 B2 | 2/2008 | Andreas et al. |
| 7,329,278 B2 | 2/2008 | Seguin et al. |
| 7,331,991 B2 | 2/2008 | Kheradvar et al. |
| 7,335,213 B1 | 2/2008 | Hyde et al. |
| 7,374,571 B2 | 5/2008 | Pease et al. |
| 7,377,941 B2 | 5/2008 | Rhee et al. |
| 7,381,210 B2 | 6/2008 | Zarbatany et al. |
| 7,381,218 B2 | 6/2008 | Schreck |
| 7,393,360 B2 | 7/2008 | Spenser et al. |
| 7,404,824 B1 | 7/2008 | Webler et al. |
| 7,416,554 B2 | 8/2008 | Lam et al. |
| 7,422,072 B2 | 9/2008 | Dade |
| 7,429,269 B2 | 9/2008 | Schwammenthal et al. |
| 7,442,204 B2 | 10/2008 | Schwammenthal et al. |
| 7,445,631 B2 | 11/2008 | Salahieh et al. |
| 7,462,191 B2 | 12/2008 | Spenser et al. |
| 7,470,285 B2 | 12/2008 | Nugent et al. |
| 7,500,989 B2 | 3/2009 | Solem et al. |
| 7,503,931 B2 | 3/2009 | Kowalsky et al. |
| 7,510,572 B2 | 3/2009 | Gabbay |
| 7,510,575 B2 | 3/2009 | Spenser et al. |
| 7,513,908 B2 | 4/2009 | Lattouf |
| 7,524,330 B2 | 4/2009 | Berreklouw |
| 7,527,647 B2 | 5/2009 | Spence |
| 7,534,260 B2 | 5/2009 | Lattouf |
| 7,556,646 B2 | 7/2009 | Yang et al. |
| 7,579,381 B2 | 8/2009 | Dove |
| 7,585,321 B2 | 9/2009 | Cribier |
| 7,591,847 B2 | 9/2009 | Navia et al. |
| 7,618,446 B2 | 11/2009 | Andersen et al. |
| 7,618,447 B2 | 11/2009 | Case et al. |
| 7,621,948 B2 | 11/2009 | Herrmann et al. |
| 7,632,304 B2 | 12/2009 | Park |
| 7,632,308 B2 | 12/2009 | Loulmet |
| 7,635,386 B1 | 12/2009 | Gammie |
| 7,674,222 B2 | 3/2010 | Nikolic et al. |
| 7,674,286 B2 | 3/2010 | Alfieri et al. |
| 7,695,510 B2 | 4/2010 | Bloom et al. |
| 7,708,775 B2 | 5/2010 | Rowe et al. |
| 7,748,389 B2 | 7/2010 | Salahieh et al. |
| 7,766,961 B2 | 8/2010 | Patel et al. |
| 7,789,909 B2 | 9/2010 | Andersen et al. |
| 7,803,168 B2 | 9/2010 | Gifford et al. |
| 7,803,184 B2 | 9/2010 | McGuckin, Jr. et al. |
| 7,803,185 B2 | 9/2010 | Gabbay |
| 7,806,928 B2 | 10/2010 | Rowe et al. |
| 7,837,727 B2 | 11/2010 | Goetz et al. |
| 7,854,762 B2 | 12/2010 | Speziali et al. |
| 7,892,281 B2 | 2/2011 | Seguin et al. |
| 7,896,915 B2 | 3/2011 | Guyenot et al. |
| 7,901,454 B2 | 3/2011 | Kapadia et al. |

(56) References Cited

U.S. PATENT DOCUMENTS

| | | |
|---|---|---|
| 7,927,370 B2 | 4/2011 | Webler et al. |
| 7,931,630 B2 | 4/2011 | Nishtala et al. |
| 7,942,928 B2 | 5/2011 | Webler et al. |
| 7,955,247 B2 | 6/2011 | Levine et al. |
| 7,955,385 B2 | 6/2011 | Crittenden |
| 7,972,378 B2 | 7/2011 | Tabor et al. |
| 7,988,727 B2 | 8/2011 | Santamore et al. |
| 7,993,394 B2 | 8/2011 | Hariton et al. |
| 8,007,992 B2 | 8/2011 | Tian et al. |
| 8,029,556 B2 | 10/2011 | Rowe |
| 8,043,368 B2 | 10/2011 | Crabtree |
| 8,052,749 B2 | 11/2011 | Salahieh et al. |
| 8,052,750 B2 | 11/2011 | Tuval et al. |
| 8,052,751 B2 | 11/2011 | Aklog et al. |
| 8,062,355 B2 | 11/2011 | Figulla et al. |
| 8,062,359 B2 | 11/2011 | Marquez et al. |
| 8,070,802 B2 | 12/2011 | Lamphere et al. |
| 8,109,996 B2 | 2/2012 | Stacchino et al. |
| 8,142,495 B2 | 3/2012 | Hasenkam et al. |
| 8,152,821 B2 | 4/2012 | Gambale et al. |
| 8,157,810 B2 | 4/2012 | Case et al. |
| 8,167,932 B2 | 5/2012 | Bourang et al. |
| 8,167,934 B2 | 5/2012 | Styrc et al. |
| 8,187,299 B2 | 5/2012 | Goldfarb et al. |
| 8,206,439 B2 | 6/2012 | Gomez Duran |
| 8,216,301 B2 | 7/2012 | Bonhoeffer et al. |
| 8,226,711 B2 | 7/2012 | Mortier et al. |
| 8,236,045 B2 | 8/2012 | Benichou et al. |
| 8,241,274 B2 | 8/2012 | Keogh et al. |
| 8,252,051 B2 | 8/2012 | Chau et al. |
| 8,303,653 B2 | 11/2012 | Bonhoeffer et al. |
| 8,308,796 B2 | 11/2012 | Lashinski et al. |
| 8,323,334 B2 | 12/2012 | Deem et al. |
| 8,353,955 B2 | 1/2013 | Styrc et al. |
| RE44,075 E | 3/2013 | Williamson et al. |
| 8,449,599 B2 | 5/2013 | Chau et al. |
| 8,454,656 B2 | 6/2013 | Tuval |
| 8,470,028 B2 | 6/2013 | Thornton et al. |
| 8,480,730 B2 | 7/2013 | Maurer et al. |
| 8,486,138 B2 | 7/2013 | Vesely |
| 8,506,623 B2 | 8/2013 | Wilson et al. |
| 8,506,624 B2 | 8/2013 | Vidlund et al. |
| 8,578,705 B2 | 11/2013 | Sindano et al. |
| 8,579,913 B2 | 11/2013 | Nielsen |
| 8,591,573 B2 | 11/2013 | Barone |
| 8,591,576 B2 | 11/2013 | Hasenkam et al. |
| 8,597,347 B2 | 12/2013 | Maurer et al. |
| 8,685,086 B2 | 4/2014 | Navia et al. |
| 8,790,394 B2 | 7/2014 | Miller et al. |
| 8,845,717 B2 | 9/2014 | Khairkhahan et al. |
| 8,888,843 B2 | 11/2014 | Khairkhahan et al. |
| 8,900,214 B2 | 12/2014 | Nance et al. |
| 8,900,295 B2 | 12/2014 | Migliazza et al. |
| 8,926,696 B2 | 1/2015 | Cabiri et al. |
| 8,932,342 B2 | 1/2015 | McHugo et al. |
| 8,932,348 B2 | 1/2015 | Solem et al. |
| 8,945,208 B2 | 2/2015 | Jimenez et al. |
| 8,956,407 B2 | 2/2015 | Macoviak et al. |
| 8,979,922 B2 | 3/2015 | Jayasinghe et al. |
| 8,986,376 B2 | 3/2015 | Solem |
| 9,011,522 B2 | 4/2015 | Annest |
| 9,023,099 B2 | 5/2015 | Duffy et al. |
| 9,034,032 B2 | 5/2015 | McLean et al. |
| 9,034,033 B2 | 5/2015 | McLean et al. |
| 9,039,757 B2 | 5/2015 | McLean et al. |
| 9,039,759 B2 | 5/2015 | Alkhatib et al. |
| 9,078,645 B2 | 7/2015 | Conklin et al. |
| 9,078,749 B2 | 7/2015 | Lutter et al. |
| 9,084,676 B2 | 7/2015 | Chau et al. |
| 9,095,433 B2 | 8/2015 | Lutter et al. |
| 9,125,742 B2 | 9/2015 | Yoganathan et al. |
| 9,149,357 B2 | 10/2015 | Seguin |
| 9,161,837 B2 | 10/2015 | Kapadia |
| 9,168,137 B2 | 10/2015 | Subramanian et al. |
| 9,232,995 B2 | 1/2016 | Kovalsky et al. |
| 9,232,998 B2 | 1/2016 | Wilson et al. |
| 9,232,999 B2 | 1/2016 | Maurer et al. |
| 9,241,702 B2 | 1/2016 | Maisano et al. |
| 9,254,192 B2 | 2/2016 | Lutter et al. |
| 9,265,608 B2 | 2/2016 | Miller et al. |
| 9,289,295 B2 | 3/2016 | Aklog et al. |
| 9,289,297 B2 | 3/2016 | Wilson et al. |
| 9,345,573 B2 | 5/2016 | Nyuli et al. |
| 9,480,557 B2 | 11/2016 | Pellegrini et al. |
| 9,480,559 B2 | 11/2016 | Vidlund et al. |
| 9,526,611 B2 | 12/2016 | Tegels et al. |
| 9,597,181 B2 | 3/2017 | Christianson et al. |
| 9,610,159 B2 | 4/2017 | Christianson et al. |
| 9,675,454 B2 | 6/2017 | Vidlund et al. |
| 9,730,792 B2 | 8/2017 | Lutter et al. |
| 9,827,092 B2 | 11/2017 | Vidlund et al. |
| 9,833,315 B2 | 12/2017 | Vidlund et al. |
| 9,867,700 B2 | 1/2018 | Bakis et al. |
| 9,883,941 B2 | 2/2018 | Hastings et al. |
| 9,895,221 B2 | 2/2018 | Vidlund |
| 9,975,750 B2 | 5/2018 | Thomas et al. |
| 9,986,993 B2 | 6/2018 | Vidlund et al. |
| 2001/0018611 A1 | 8/2001 | Solem et al. |
| 2001/0021872 A1 | 9/2001 | Bailey et al. |
| 2001/0025171 A1 | 9/2001 | Mortier et al. |
| 2002/0010427 A1 | 1/2002 | Scarfone et al. |
| 2002/0032481 A1 | 3/2002 | Gabbay |
| 2002/0116054 A1 | 8/2002 | Lundell et al. |
| 2002/0138138 A1 | 9/2002 | Yang |
| 2002/0139056 A1 | 10/2002 | Finnell |
| 2002/0151961 A1 | 10/2002 | Lashinski et al. |
| 2002/0161377 A1 | 10/2002 | Rabkin |
| 2002/0173842 A1 | 11/2002 | Buchanan |
| 2002/0183827 A1 | 12/2002 | Derus et al. |
| 2003/0010509 A1 | 1/2003 | Hoffman |
| 2003/0036698 A1 | 2/2003 | Kohler et al. |
| 2003/0050694 A1 | 3/2003 | Yang et al. |
| 2003/0078652 A1 | 4/2003 | Sutherland |
| 2003/0100939 A1 | 5/2003 | Yodfat et al. |
| 2003/0105519 A1 | 6/2003 | Fasol et al. |
| 2003/0105520 A1 | 6/2003 | Alferness et al. |
| 2003/0120340 A1 | 6/2003 | Liska et al. |
| 2003/0130731 A1 | 7/2003 | Vidlund et al. |
| 2003/0149476 A1 | 8/2003 | Damm et al. |
| 2003/0212454 A1 | 11/2003 | Scott et al. |
| 2004/0039436 A1 | 2/2004 | Spenser et al. |
| 2004/0049266 A1 | 3/2004 | Anduiza et al. |
| 2004/0064014 A1 | 4/2004 | Melvin et al. |
| 2004/0092858 A1 | 5/2004 | Wilson et al. |
| 2004/0093075 A1 | 5/2004 | Kuehne |
| 2004/0097865 A1 | 5/2004 | Anderson et al. |
| 2004/0127983 A1 | 7/2004 | Mortier et al. |
| 2004/0133263 A1 | 7/2004 | Dusbabek et al. |
| 2004/0147958 A1 | 7/2004 | Lam et al. |
| 2004/0152947 A1 | 8/2004 | Schroeder et al. |
| 2004/0162610 A1 | 8/2004 | Liska et al. |
| 2004/0163828 A1 | 8/2004 | Silverstein et al. |
| 2004/0181239 A1 | 9/2004 | Dorn et al. |
| 2004/0186565 A1 | 9/2004 | Schreck |
| 2004/0186566 A1 | 9/2004 | Hindrichs et al. |
| 2004/0260317 A1 | 12/2004 | Bloom et al. |
| 2004/0260389 A1 | 12/2004 | Case et al. |
| 2005/0004652 A1 | 1/2005 | van der Burg et al. |
| 2005/0004666 A1 | 1/2005 | Alfieri et al. |
| 2005/0075727 A1 | 4/2005 | Wheatley |
| 2005/0080402 A1 | 4/2005 | Santamore et al. |
| 2005/0085900 A1 | 4/2005 | Case et al. |
| 2005/0096498 A1 | 5/2005 | Houser et al. |
| 2005/0107661 A1 | 5/2005 | Lau et al. |
| 2005/0113798 A1 | 5/2005 | Slater et al. |
| 2005/0113810 A1 | 5/2005 | Houser et al. |
| 2005/0113811 A1 | 5/2005 | Houser et al. |
| 2005/0119519 A9 | 6/2005 | Girard et al. |
| 2005/0121206 A1 | 6/2005 | Dolan |
| 2005/0125012 A1 | 6/2005 | Houser et al. |
| 2005/0137686 A1 | 6/2005 | Salahieh et al. |
| 2005/0137688 A1 | 6/2005 | Salahieh et al. |
| 2005/0137695 A1 | 6/2005 | Salahieh et al. |
| 2005/0137698 A1 | 6/2005 | Salahieh et al. |

(56) References Cited

U.S. PATENT DOCUMENTS

| | | |
|---|---|---|
| 2005/0148815 A1 | 7/2005 | Mortier et al. |
| 2005/0177180 A1 | 8/2005 | Kaganov et al. |
| 2005/0197695 A1 | 9/2005 | Stacchino et al. |
| 2005/0203614 A1 | 9/2005 | Forster et al. |
| 2005/0203615 A1 | 9/2005 | Forster et al. |
| 2005/0203617 A1 | 9/2005 | Forster et al. |
| 2005/0234546 A1 | 10/2005 | Nugent et al. |
| 2005/0240200 A1 | 10/2005 | Bergheim |
| 2005/0251209 A1 | 11/2005 | Saadat et al. |
| 2005/0256567 A1 | 11/2005 | Lim et al. |
| 2005/0283231 A1 | 12/2005 | Haug et al. |
| 2005/0288766 A1 | 12/2005 | Plain et al. |
| 2006/0004442 A1 | 1/2006 | Spenser et al. |
| 2006/0025784 A1 | 2/2006 | Starksen et al. |
| 2006/0025857 A1 | 2/2006 | Bergheim et al. |
| 2006/0030885 A1 | 2/2006 | Hyde |
| 2006/0042803 A1 | 3/2006 | Gallaher |
| 2006/0047338 A1 | 3/2006 | Jenson et al. |
| 2006/0052868 A1 | 3/2006 | Mortier et al. |
| 2006/0058872 A1 | 3/2006 | Salahieh et al. |
| 2006/0094983 A1 | 5/2006 | Burbank et al. |
| 2006/0129025 A1 | 6/2006 | Levine et al. |
| 2006/0142784 A1 | 6/2006 | Kontos |
| 2006/0149350 A1 | 7/2006 | Patel et al. |
| 2006/0161040 A1 | 7/2006 | McCarthy et al. |
| 2006/0161249 A1 | 7/2006 | Realyvasquez et al. |
| 2006/0167541 A1 | 7/2006 | Lattouf |
| 2006/0195134 A1 | 8/2006 | Crittenden |
| 2006/0195183 A1 | 8/2006 | Navia et al. |
| 2006/0229708 A1 | 10/2006 | Powell et al. |
| 2006/0229719 A1 | 10/2006 | Marquez et al. |
| 2006/0241745 A1 | 10/2006 | Solem |
| 2006/0247491 A1 | 11/2006 | Vidlund et al. |
| 2006/0252984 A1 | 11/2006 | Rahdert et al. |
| 2006/0259135 A1 | 11/2006 | Navia et al. |
| 2006/0259136 A1 | 11/2006 | Nguyen et al. |
| 2006/0259137 A1 | 11/2006 | Artof et al. |
| 2006/0276874 A1 | 12/2006 | Wilson et al. |
| 2006/0282161 A1 | 12/2006 | Huynh et al. |
| 2006/0287716 A1 | 12/2006 | Banbury et al. |
| 2006/0287717 A1 | 12/2006 | Rowe et al. |
| 2007/0005131 A1 | 1/2007 | Taylor |
| 2007/0005231 A1 | 1/2007 | Seguchi |
| 2007/0010877 A1 | 1/2007 | Salahieh et al. |
| 2007/0016286 A1 | 1/2007 | Herrmann et al. |
| 2007/0016288 A1 | 1/2007 | Gurskis et al. |
| 2007/0027535 A1 | 2/2007 | Purdy et al. |
| 2007/0038291 A1 | 2/2007 | Case et al. |
| 2007/0050020 A1 | 3/2007 | Spence |
| 2007/0061010 A1 | 3/2007 | Hauser et al. |
| 2007/0066863 A1 | 3/2007 | Rafiee et al. |
| 2007/0073387 A1 | 3/2007 | Forster et al. |
| 2007/0078297 A1 | 4/2007 | Rafiee et al. |
| 2007/0083076 A1 | 4/2007 | Lichtenstein |
| 2007/0083259 A1 | 4/2007 | Bloom et al. |
| 2007/0093890 A1 | 4/2007 | Eliasen et al. |
| 2007/0100439 A1 | 5/2007 | Cangialosi et al. |
| 2007/0112422 A1 | 5/2007 | Dehdashtian |
| 2007/0112425 A1 | 5/2007 | Schaller et al. |
| 2007/0118151 A1 | 5/2007 | Davidson |
| 2007/0118154 A1 | 5/2007 | Crabtree |
| 2007/0118210 A1 | 5/2007 | Pinchuk |
| 2007/0118213 A1 | 5/2007 | Loulmet |
| 2007/0142906 A1 | 6/2007 | Figulla et al. |
| 2007/0161846 A1 | 7/2007 | Nikolic et al. |
| 2007/0162048 A1 | 7/2007 | Quinn et al. |
| 2007/0162103 A1 | 7/2007 | Case et al. |
| 2007/0162111 A1* | 7/2007 | Fukamachi ............ A61F 2/2412 623/2.11 |
| 2007/0168024 A1 | 7/2007 | Khairkhahan |
| 2007/0185565 A1 | 8/2007 | Schwammenthal et al. |
| 2007/0185571 A1 | 8/2007 | Kapadia et al. |
| 2007/0203575 A1 | 8/2007 | Forster et al. |
| 2007/0213813 A1 | 9/2007 | Von Segesser et al. |
| 2007/0215362 A1 | 9/2007 | Rodgers |
| 2007/0221388 A1 | 9/2007 | Johnson |
| 2007/0233239 A1 | 10/2007 | Navia et al. |
| 2007/0239265 A1 | 10/2007 | Birdsall |
| 2007/0256843 A1 | 11/2007 | Pahila |
| 2007/0265658 A1 | 11/2007 | Nelson et al. |
| 2007/0267202 A1 | 11/2007 | Mariller |
| 2007/0270932 A1 | 11/2007 | Headley et al. |
| 2007/0270943 A1 | 11/2007 | Solem et al. |
| 2007/0293944 A1 | 12/2007 | Spenser et al. |
| 2008/0009940 A1 | 1/2008 | Cribier |
| 2008/0033543 A1 | 2/2008 | Gurskis et al. |
| 2008/0065011 A1 | 3/2008 | Marchand et al. |
| 2008/0071361 A1 | 3/2008 | Tuval et al. |
| 2008/0071362 A1 | 3/2008 | Tuval et al. |
| 2008/0071363 A1 | 3/2008 | Tuval et al. |
| 2008/0071366 A1 | 3/2008 | Tuval et al. |
| 2008/0071368 A1 | 3/2008 | Tuval et al. |
| 2008/0071369 A1 | 3/2008 | Tuval et al. |
| 2008/0082163 A1 | 4/2008 | Woo |
| 2008/0082166 A1 | 4/2008 | Styrc et al. |
| 2008/0091264 A1 | 4/2008 | Machold et al. |
| 2008/0114442 A1 | 5/2008 | Mitchell et al. |
| 2008/0125861 A1 | 5/2008 | Webler et al. |
| 2008/0147179 A1 | 6/2008 | Cai et al. |
| 2008/0154355 A1 | 6/2008 | Benichou et al. |
| 2008/0154356 A1 | 6/2008 | Obermiller et al. |
| 2008/0161911 A1 | 7/2008 | Revuelta et al. |
| 2008/0172035 A1 | 7/2008 | Starksen et al. |
| 2008/0177381 A1 | 7/2008 | Navia et al. |
| 2008/0183203 A1 | 7/2008 | Fitzgerald et al. |
| 2008/0183273 A1 | 7/2008 | Mesana et al. |
| 2008/0188928 A1 | 8/2008 | Salahieh et al. |
| 2008/0208328 A1 | 8/2008 | Antocci et al. |
| 2008/0208332 A1 | 8/2008 | Lamphere et al. |
| 2008/0221672 A1 | 9/2008 | Lamphere et al. |
| 2008/0243150 A1 | 10/2008 | Starksen et al. |
| 2008/0243245 A1 | 10/2008 | Thambar et al. |
| 2008/0255660 A1 | 10/2008 | Guyenot et al. |
| 2008/0255661 A1 | 10/2008 | Straubinger et al. |
| 2008/0281411 A1 | 11/2008 | Berreklouw |
| 2008/0288060 A1 | 11/2008 | Kaye et al. |
| 2008/0293996 A1 | 11/2008 | Evans et al. |
| 2009/0005863 A1 | 1/2009 | Goetz et al. |
| 2009/0048668 A1 | 2/2009 | Wilson et al. |
| 2009/0054968 A1 | 2/2009 | Bonhoeffer et al. |
| 2009/0054974 A1 | 2/2009 | McGuckin, Jr. et al. |
| 2009/0062908 A1 | 3/2009 | Bonhoeffer et al. |
| 2009/0076598 A1 | 3/2009 | Salahieh et al. |
| 2009/0082619 A1 | 3/2009 | De Marchena |
| 2009/0088836 A1 | 4/2009 | Bishop et al. |
| 2009/0099410 A1 | 4/2009 | De Marchena |
| 2009/0112309 A1 | 4/2009 | Jaramillo et al. |
| 2009/0131849 A1 | 5/2009 | Maurer et al. |
| 2009/0132035 A1 | 5/2009 | Roth et al. |
| 2009/0137861 A1 | 5/2009 | Goldberg et al. |
| 2009/0138079 A1 | 5/2009 | Tuval et al. |
| 2009/0157175 A1 | 6/2009 | Benichou |
| 2009/0164005 A1 | 6/2009 | Dove et al. |
| 2009/0171432 A1 | 7/2009 | Von Segesser et al. |
| 2009/0171447 A1 | 7/2009 | Von Segesser et al. |
| 2009/0171456 A1 | 7/2009 | Kveen et al. |
| 2009/0177266 A1 | 7/2009 | Powell et al. |
| 2009/0192601 A1 | 7/2009 | Rafiee et al. |
| 2009/0210052 A1 | 8/2009 | Forster et al. |
| 2009/0216322 A1 | 8/2009 | Le et al. |
| 2009/0222076 A1 | 9/2009 | Figulla et al. |
| 2009/0224529 A1 | 9/2009 | Gill |
| 2009/0234318 A1 | 9/2009 | Loulmet et al. |
| 2009/0234435 A1 | 9/2009 | Johnson et al. |
| 2009/0234443 A1 | 9/2009 | Ottma et al. |
| 2009/0240320 A1 | 9/2009 | Tuval et al. |
| 2009/0248149 A1 | 10/2009 | Gabbay |
| 2009/0276040 A1 | 11/2009 | Rowe et al. |
| 2009/0281619 A1 | 11/2009 | Le et al. |
| 2009/0287299 A1 | 11/2009 | Tabor et al. |
| 2009/0292262 A1 | 11/2009 | Adams et al. |
| 2009/0319037 A1 | 12/2009 | Rowe et al. |
| 2009/0326575 A1 | 12/2009 | Galdonik et al. |
| 2010/0016958 A1 | 1/2010 | St. Goar et al. |

(56) References Cited

U.S. PATENT DOCUMENTS

| | | |
|---|---|---|
| 2010/0021382 A1 | 1/2010 | Dorshow et al. |
| 2010/0023117 A1 | 1/2010 | Yoganathan et al. |
| 2010/0036479 A1 | 2/2010 | Hill et al. |
| 2010/0049313 A1 | 2/2010 | Alon et al. |
| 2010/0082094 A1 | 4/2010 | Quadri et al. |
| 2010/0161041 A1 | 6/2010 | Maisano et al. |
| 2010/0168839 A1 | 7/2010 | Braido et al. |
| 2010/0179641 A1 | 7/2010 | Ryan et al. |
| 2010/0185277 A1 | 7/2010 | Braido et al. |
| 2010/0185278 A1 | 7/2010 | Schankereli |
| 2010/0191326 A1 | 7/2010 | Alkhatib |
| 2010/0192402 A1 | 8/2010 | Yamaguchi et al. |
| 2010/0204781 A1 | 8/2010 | Alkhatib |
| 2010/0210899 A1 | 8/2010 | Schankereli |
| 2010/0217382 A1 | 8/2010 | Chau et al. |
| 2010/0249489 A1 | 9/2010 | Jarvik |
| 2010/0249923 A1 | 9/2010 | Alkhatib et al. |
| 2010/0280604 A1 | 11/2010 | Zipory et al. |
| 2010/0286768 A1 | 11/2010 | Alkhatib |
| 2010/0298755 A1 | 11/2010 | McNamara et al. |
| 2010/0298931 A1 | 11/2010 | Quadri et al. |
| 2010/0324554 A1 | 12/2010 | Gifford et al. |
| 2011/0004296 A1 | 1/2011 | Lutter et al. |
| 2011/0015616 A1 | 1/2011 | Straubinger et al. |
| 2011/0015728 A1 | 1/2011 | Jimenez et al. |
| 2011/0015729 A1 | 1/2011 | Jimenez et al. |
| 2011/0029072 A1 | 2/2011 | Gabbay |
| 2011/0066231 A1 | 3/2011 | Cartledge et al. |
| 2011/0066233 A1 | 3/2011 | Thornton et al. |
| 2011/0112632 A1 | 5/2011 | Chau et al. |
| 2011/0137397 A1 | 6/2011 | Chau et al. |
| 2011/0137408 A1 | 6/2011 | Bergheim |
| 2011/0224655 A1 | 9/2011 | Asirvatham et al. |
| 2011/0224678 A1 | 9/2011 | Gabbay |
| 2011/0224728 A1 | 9/2011 | Martin et al. |
| 2011/0224784 A1 | 9/2011 | Quinn |
| 2011/0245911 A1 | 10/2011 | Quill et al. |
| 2011/0251682 A1 | 10/2011 | Murray, III et al. |
| 2011/0264191 A1 | 10/2011 | Rothstein |
| 2011/0264206 A1 | 10/2011 | Tabor |
| 2011/0288637 A1 | 11/2011 | Marchena |
| 2011/0319988 A1 | 12/2011 | Schankereli et al. |
| 2011/0319989 A1 | 12/2011 | Lane et al. |
| 2012/0010694 A1 | 1/2012 | Lutter et al. |
| 2012/0016468 A1 | 1/2012 | Robin et al. |
| 2012/0022640 A1 | 1/2012 | Gross et al. |
| 2012/0035703 A1 | 2/2012 | Lutter et al. |
| 2012/0035713 A1 | 2/2012 | Lutter et al. |
| 2012/0035722 A1 | 2/2012 | Tuval |
| 2012/0053686 A1 | 3/2012 | McNamara et al. |
| 2012/0059487 A1 | 3/2012 | Cunanan et al. |
| 2012/0089171 A1 | 4/2012 | Hastings et al. |
| 2012/0101571 A1 | 4/2012 | Thambar et al. |
| 2012/0101572 A1 | 4/2012 | Kovalsky et al. |
| 2012/0116351 A1 | 5/2012 | Chomas et al. |
| 2012/0123529 A1 | 5/2012 | Levi et al. |
| 2012/0158129 A1 | 6/2012 | Duffy et al. |
| 2012/0165930 A1 | 6/2012 | Gifford et al. |
| 2012/0179244 A1 | 7/2012 | Schankereli et al. |
| 2012/0203336 A1 | 8/2012 | Annest |
| 2012/0215303 A1 | 8/2012 | Quadri et al. |
| 2012/0226348 A1 | 9/2012 | Lane et al. |
| 2012/0283824 A1 | 11/2012 | Lutter et al. |
| 2012/0289945 A1 | 11/2012 | Segermark |
| 2013/0030522 A1 | 1/2013 | Rowe et al. |
| 2013/0053950 A1 | 2/2013 | Rowe et al. |
| 2013/0066341 A1 | 3/2013 | Ketai et al. |
| 2013/0079873 A1 | 3/2013 | Migliazza et al. |
| 2013/0131788 A1 | 5/2013 | Quadri et al. |
| 2013/0172978 A1 | 7/2013 | Vidlund et al. |
| 2013/0184811 A1 | 7/2013 | Rowe et al. |
| 2013/0190860 A1 | 7/2013 | Sundt, III |
| 2013/0190861 A1 | 7/2013 | Chau et al. |
| 2013/0197622 A1 | 8/2013 | Mitra et al. |
| 2013/0226288 A1 | 8/2013 | Goldwasser et al. |
| 2013/0231735 A1 | 9/2013 | Deem et al. |
| 2013/0274874 A1 | 10/2013 | Hammer |
| 2013/0282101 A1 | 10/2013 | Eidenschink et al. |
| 2013/0310928 A1 | 11/2013 | Morriss et al. |
| 2013/0317603 A1 | 11/2013 | McLean et al. |
| 2013/0325041 A1 | 12/2013 | Annest et al. |
| 2013/0325110 A1 | 12/2013 | Khalil et al. |
| 2013/0338752 A1 | 12/2013 | Geusen et al. |
| 2013/0345715 A1 | 12/2013 | Gifford et al. |
| 2014/0046433 A1 | 2/2014 | Kovalsky |
| 2014/0081323 A1 | 3/2014 | Hawkins |
| 2014/0094918 A1 | 4/2014 | Vishnubholta et al. |
| 2014/0142691 A1 | 5/2014 | Pouletty |
| 2014/0163668 A1 | 6/2014 | Rafiee |
| 2014/0194981 A1 | 7/2014 | Menk et al. |
| 2014/0194983 A1 | 7/2014 | Kovalsky et al. |
| 2014/0214159 A1 | 7/2014 | Vidlund et al. |
| 2014/0222142 A1 | 8/2014 | Kovalsky et al. |
| 2014/0243966 A1 | 8/2014 | Garde et al. |
| 2014/0277419 A1 | 9/2014 | Garde et al. |
| 2014/0296969 A1 | 10/2014 | Tegels et al. |
| 2014/0296970 A1 | 10/2014 | Ekvall et al. |
| 2014/0296971 A1 | 10/2014 | Tegels et al. |
| 2014/0296972 A1 | 10/2014 | Tegels et al. |
| 2014/0296975 A1 | 10/2014 | Tegels et al. |
| 2014/0303718 A1 | 10/2014 | Tegels et al. |
| 2014/0309732 A1 | 10/2014 | Solem |
| 2014/0316516 A1 | 10/2014 | Vidlund et al. |
| 2014/0324160 A1 | 10/2014 | Benichou et al. |
| 2014/0324161 A1 | 10/2014 | Tegels et al. |
| 2014/0324164 A1 | 10/2014 | Gross et al. |
| 2014/0331475 A1 | 11/2014 | Duffy et al. |
| 2014/0358224 A1 | 12/2014 | Tegels et al. |
| 2014/0364942 A1 | 12/2014 | Straubinger et al. |
| 2014/0364944 A1 | 12/2014 | Lutter et al. |
| 2014/0379076 A1 | 12/2014 | Vidlund et al. |
| 2015/0005874 A1 | 1/2015 | Vidlund et al. |
| 2015/0011821 A1 | 1/2015 | Gorman et al. |
| 2015/0025553 A1 | 1/2015 | Del Nido et al. |
| 2015/0057705 A1 | 2/2015 | Vidlund |
| 2015/0073542 A1 | 3/2015 | Heldman |
| 2015/0073545 A1 | 3/2015 | Braido |
| 2015/0094802 A1 | 4/2015 | Buchbinder et al. |
| 2015/0105856 A1 | 4/2015 | Rowe et al. |
| 2015/0119936 A1 | 4/2015 | Gilmore et al. |
| 2015/0119978 A1 | 4/2015 | Tegels et al. |
| 2015/0127093 A1 | 5/2015 | Hosmer et al. |
| 2015/0127096 A1 | 5/2015 | Rowe et al. |
| 2015/0134050 A1 | 5/2015 | Solem et al. |
| 2015/0142100 A1 | 5/2015 | Morriss et al. |
| 2015/0142101 A1 | 5/2015 | Coleman et al. |
| 2015/0142103 A1 | 5/2015 | Vidlund |
| 2015/0142104 A1 | 5/2015 | Braido |
| 2015/0173897 A1 | 6/2015 | Raanani et al. |
| 2015/0196393 A1 | 7/2015 | Vidlund et al. |
| 2015/0196688 A1 | 7/2015 | James |
| 2015/0202044 A1 | 7/2015 | Chau et al. |
| 2015/0216653 A1 | 8/2015 | Freudenthal |
| 2015/0216660 A1 | 8/2015 | Pintor |
| 2015/0223820 A1 | 8/2015 | Olson |
| 2015/0223934 A1 | 8/2015 | Vidlund et al. |
| 2015/0238312 A1 | 8/2015 | Lashinski |
| 2015/0238729 A1 | 8/2015 | Jenson et al. |
| 2015/0272731 A1 | 10/2015 | Racchini et al. |
| 2015/0305860 A1 | 10/2015 | Wang et al. |
| 2015/0305864 A1 | 10/2015 | Quadri et al. |
| 2015/0305868 A1 | 10/2015 | Lutter et al. |
| 2015/0327995 A1 | 11/2015 | Morin et al. |
| 2015/0328001 A1 | 11/2015 | McLean |
| 2015/0335424 A1 | 11/2015 | McLean |
| 2015/0335429 A1 | 11/2015 | Morriss et al. |
| 2015/0342717 A1 | 12/2015 | O'Donnell et al. |
| 2015/0351903 A1 | 12/2015 | Morriss et al. |
| 2015/0351906 A1 | 12/2015 | Hammer et al. |
| 2016/0000562 A1 | 1/2016 | Siegel |
| 2016/0008131 A1 | 1/2016 | Christianson et al. |
| 2016/0067042 A1 | 3/2016 | Murad et al. |
| 2016/0074160 A1 | 3/2016 | Christianson et al. |
| 2016/0106537 A1 | 4/2016 | Christianson et al. |

(56) References Cited

U.S. PATENT DOCUMENTS

| | | |
|---|---|---|
| 2016/0113764 A1 | 4/2016 | Sheahan |
| 2016/0143736 A1 | 5/2016 | Vidlund |
| 2016/0151155 A1 | 6/2016 | Lutter et al. |
| 2016/0206280 A1 | 7/2016 | Vidlund et al. |
| 2016/0242902 A1 | 8/2016 | Morriss |
| 2016/0262879 A1 | 9/2016 | Meiri et al. |
| 2016/0262881 A1 | 9/2016 | Schankereli et al. |
| 2016/0278955 A1 | 9/2016 | Liu et al. |
| 2016/0317290 A1 | 11/2016 | Chau |
| 2016/0324635 A1 | 11/2016 | Vidlund et al. |
| 2016/0331527 A1 | 11/2016 | Vidlund et al. |
| 2016/0346086 A1 | 12/2016 | Solem |
| 2016/0367365 A1 | 12/2016 | Conklin |
| 2016/0367367 A1 | 12/2016 | Maisano et al. |
| 2016/0367368 A1 | 12/2016 | Vidlund et al. |
| 2017/0079790 A1 | 3/2017 | Vidlund et al. |
| 2017/0100248 A1 | 4/2017 | Tegels et al. |
| 2017/0128208 A1 | 5/2017 | Christianson et al. |
| 2017/0181854 A1 | 6/2017 | Christianson et al. |
| 2017/0196688 A1 | 7/2017 | Christianson et al. |
| 2017/0252153 A1 | 9/2017 | Chau et al. |
| 2017/0266001 A1 | 9/2017 | Vidlund et al. |
| 2017/0281343 A1 | 10/2017 | Christianson et al. |
| 2017/0312077 A1 | 11/2017 | Vidlund et al. |
| 2017/0319333 A1 | 11/2017 | Tegels et al. |
| 2018/0028314 A1 | 2/2018 | Ekvall et al. |
| 2018/0078368 A1 | 3/2018 | Vidlund et al. |
| 2018/0078370 A1 | 3/2018 | Kovalsky et al. |
| 2018/0147055 A1 | 5/2018 | Vidlund et al. |
| 2018/0193138 A1 | 7/2018 | Vidlund |
| 2018/0263618 A1 | 9/2018 | Vidlund et al. |
| 2018/0271653 A1 | 9/2018 | Vidlund et al. |

FOREIGN PATENT DOCUMENTS

| | | |
|---|---|---|
| CN | 2902226 Y | 5/2007 |
| CN | 101146484 A | 3/2008 |
| CN | 101180010 A | 5/2008 |
| CN | 101984938 A | 3/2011 |
| CN | 102869317 A | 1/2013 |
| CN | 102869318 A | 1/2013 |
| CN | 102869321 A | 1/2013 |
| CN | 103220993 A | 7/2013 |
| CN | 102639179 B | 10/2014 |
| DE | 1001074 B | 1/1957 |
| DE | 2246526 A1 | 3/1973 |
| DE | 19532846 A1 | 3/1997 |
| DE | 19546692 A1 | 6/1997 |
| DE | 19857887 A1 | 7/2000 |
| DE | 19907646 A1 | 8/2000 |
| DE | 10010074 A1 | 10/2001 |
| DE | 10049812 A1 | 4/2002 |
| DE | 10049813 C1 | 4/2002 |
| DE | 10049814 | 4/2002 |
| DE | 10049815 A1 | 4/2002 |
| DE | 102006052564 B3 | 12/2007 |
| DE | 102006052710 A1 | 5/2008 |
| DE | 102007043830 A1 | 4/2009 |
| DE | 102007043831 A1 | 4/2009 |
| EP | 0103546 A1 | 3/1984 |
| EP | 0144167 | 6/1985 |
| EP | 0592410 A1 | 4/1994 |
| EP | 0850607 A1 | 7/1998 |
| EP | 0597967 B1 | 12/1999 |
| EP | 1057460 A1 | 12/2000 |
| EP | 1088529 A2 | 4/2001 |
| EP | 1264582 A2 | 12/2002 |
| EP | 1570809 A1 | 9/2005 |
| EP | 1469797 B1 | 11/2005 |
| EP | 1653888 A2 | 5/2006 |
| EP | 2111800 A1 | 10/2009 |
| EP | 2193762 A1 | 6/2010 |
| EP | 2278944 A2 | 2/2011 |
| EP | 2055266 B1 | 2/2012 |
| EP | 2747707 A1 | 7/2014 |
| EP | 2918248 A1 | 9/2015 |
| FR | 2788217 A1 | 7/2000 |
| FR | 2815844 A1 | 5/2002 |
| GB | 2056023 | 3/1981 |
| JP | 2003505146 A | 2/2003 |
| JP | 2005505343 A | 2/2005 |
| JP | 2005515836 A | 6/2005 |
| JP | 2008537891 A | 10/2008 |
| JP | 2009514628 A | 4/2009 |
| JP | 2009519783 A | 5/2009 |
| JP | 2013512765 A | 4/2013 |
| NL | 1017275 C2 | 8/2002 |
| SU | 1271508 A1 | 11/1986 |
| WO | 9117720 A1 | 11/1991 |
| WO | 9217118 A1 | 10/1992 |
| WO | 9301768 A1 | 2/1993 |
| WO | 9724080 A1 | 7/1997 |
| WO | 9829057 A1 | 7/1998 |
| WO | 9933414 | 7/1999 |
| WO | 9940964 A1 | 8/1999 |
| WO | 9947075 A1 | 9/1999 |
| WO | 2000018333 A1 | 4/2000 |
| WO | 2000030550 A1 | 6/2000 |
| WO | 200041652 A1 | 7/2000 |
| WO | 200044313 A1 | 8/2000 |
| WO | 200047139 A1 | 8/2000 |
| WO | 2001035878 A2 | 5/2001 |
| WO | 2001049213 A2 | 7/2001 |
| WO | 200162189 A1 | 8/2001 |
| WO | 2001054624 A1 | 8/2001 |
| WO | 2001054625 A1 | 8/2001 |
| WO | 2001056512 A1 | 8/2001 |
| WO | 2001061289 A1 | 8/2001 |
| WO | 0164137 A1 | 9/2001 |
| WO | 200176510 A2 | 10/2001 |
| WO | 2001082840 A1 | 11/2001 |
| WO | 2002004757 A1 | 1/2002 |
| WO | 2002022054 A1 | 3/2002 |
| WO | 2002028321 A2 | 4/2002 |
| WO | 2002036048 A1 | 5/2002 |
| WO | 2002041789 A2 | 5/2002 |
| WO | 0247575 A2 | 6/2002 |
| WO | 2002043620 A1 | 6/2002 |
| WO | 2002049540 A2 | 6/2002 |
| WO | 2002076348 A1 | 10/2002 |
| WO | 2003003943 A2 | 1/2003 |
| WO | 2003003949 A2 | 1/2003 |
| WO | 2003030776 A2 | 4/2003 |
| WO | 03037227 | 5/2003 |
| WO | 03047468 A1 | 6/2003 |
| WO | 2003049619 A2 | 6/2003 |
| WO | 2004019825 A1 | 3/2004 |
| WO | 2005087140 A1 | 9/2005 |
| WO | 2005102181 A1 | 11/2005 |
| WO | 2006014233 A2 | 2/2006 |
| WO | 2006034008 A2 | 3/2006 |
| WO | 2006063199 A2 | 6/2006 |
| WO | 2006064490 A1 | 6/2006 |
| WO | 2006070372 A2 | 7/2006 |
| WO | 2006105009 A1 | 10/2006 |
| WO | 2006113906 A1 | 10/2006 |
| WO | 2006127756 A2 | 11/2006 |
| WO | 2006135536 A2 | 12/2006 |
| WO | 2007081412 A1 | 7/2007 |
| WO | 2007100408 A2 | 9/2007 |
| WO | 2007131513 A1 | 11/2007 |
| WO | 2008005405 A1 | 1/2008 |
| WO | 2008009940 A2 | 1/2008 |
| WO | 2008035337 A2 | 3/2008 |
| WO | 2008091515 A2 | 7/2008 |
| WO | 2008125906 A2 | 10/2008 |
| WO | 2008147964 A1 | 12/2008 |
| WO | 2008150529 A1 | 12/2008 |
| WO | 2009024859 A2 | 2/2009 |
| WO | 2009026272 A1 | 2/2009 |
| WO | 2009026563 A2 | 2/2009 |
| WO | 2009033469 A1 | 3/2009 |
| WO | 2009045338 A1 | 4/2009 |
| WO | 2009132187 A1 | 10/2009 |

(56) References Cited

FOREIGN PATENT DOCUMENTS

| | | | |
|---|---|---|---|
| WO | 2010090878 A2 | 8/2010 | |
| WO | 2010091653 A1 | 8/2010 | |
| WO | 2010098857 A1 | 9/2010 | |
| WO | 2010121076 A2 | 10/2010 | |
| WO | 2011017440 A2 | 2/2011 | |
| WO | 2011022658 A1 | 2/2011 | |
| WO | 2011069048 A2 | 6/2011 | |
| WO | 2011072084 A2 | 6/2011 | |
| WO | 2011106735 A1 | 9/2011 | |
| WO | 2011109813 A2 | 9/2011 | |
| WO | 2011159342 A1 | 12/2011 | |
| WO | 2011163275 A2 | 12/2011 | |
| WO | 2012027487 A2 | 3/2012 | |
| WO | 2012036742 A2 | 3/2012 | |
| WO | 2012095116 A1 | 7/2012 | |
| WO | 2012177942 A2 | 12/2012 | |
| WO | 2013/028387 A2 | 2/2013 | |
| WO | 2013021374 A2 | 2/2013 | |
| WO | 2013045262 A1 | 4/2013 | |
| WO | 2013059747 A1 | 4/2013 | |
| WO | 2013096411 A1 | 6/2013 | |
| WO | 2013103612 A1 | 7/2013 | |
| WO | 2013175468 A2 | 11/2013 | |
| WO | 2014021905 A1 | 2/2014 | |
| WO | 2014022124 A1 | 2/2014 | |
| WO | 2014121280 A2 | 8/2014 | |
| WO | 2014144937 A2 | 9/2014 | |
| WO | 2014162306 A2 | 10/2014 | |
| WO | 2014189974 A1 | 11/2014 | |
| WO | 2015051430 A1 | 4/2015 | |
| WO | 2015058039 A1 | 4/2015 | |
| WO | 2015063580 A2 | 5/2015 | |
| WO | 2015065646 A1 | 5/2015 | |
| WO | 2015120122 A2 | 8/2015 | |
| WO | 2015138306 A2 | 9/2015 | |
| WO | 2015173609 A1 | 11/2015 | |
| WO | 2016112085 A2 | 7/2016 | |
| WO | 2016126942 A2 | 8/2016 | |
| WO | 2016168609 A1 | 10/2016 | |
| WO | 2016196933 A1 | 12/2016 | |
| WO | 2017096157 A1 | 6/2017 | |
| WO | 2017132008 A1 | 8/2017 | |
| WO | 2017218375 A1 | 12/2017 | |
| WO | 2018005779 A1 | 1/2018 | |
| WO | 2018013515 A1 | 1/2018 | |

OTHER PUBLICATIONS

Kolata, G., "Device That Opens Clogged Arteries Gets a Failing Grade in a New Study," New York Times [online], <http://www.nytimes.com/1991/01/03/health/device-that-opens-clogged-ar-teries-gets-a-faili . . . ,>, published Jan. 3, 1991,retrieved from the Internet on Feb. 5, 2016, 3 pages.

Kolata, Gina, "Device That Opens Clogged Arteries Gets a Failing Grade in a New Study," nytimes.com , httol/www.nytimes.com/1991/01/03/healthidevice-that-opens-clogged-arterie- s-oets-a-faili . . . , Jul. 29, 2009, 2 pages.

L. L. Knudsen et al., "Catheter-Implanted Prosthetic Heart Valves. Transluminal Catheter Implantation of a New Expandable Artificial Heart Valve in the Descending Thoracic Aorta in Isolated Vessels and Closed Chest Pigs," International Journal ofArtificial Organs, 1993, Issue 5, vol. 16, pp. 253-262.

Lawrence, D. D., "Percutaneous Endovascular Graft: Experimental Evaluation," Radiology, 1987,163:357-360.

Lozonschi, L., et al. "Transapical mitral valved stent implantation: A survival series in swine," The Journal of Thoracic and Cardiovascular Surgery, 140(2):422-426 (Aug. 2010) published online Mar. 12, 2010, 1 page.

Lutter, Georg, et al., Mitral valved stent implantation, European Journal of Cardio-Thoracic Surgery, 2010, vol. 38, pp. 350-355.

M. Tofeig, et al., "Transcatheter Closure of Mid-Muscular Ventricular Septal Defect with an Amplatzer VSD Occluder Device," Heart, vol. 81, 1999, pp. 438-440.

Ma, L. et al., "Double-crowned valved stents for off-pump mitral valve replacement," European Journal of Cardio-Thoracic Surgery, Aug. 2005, 28(2): 194-198.

Moazami, N. et al., "Transluminal aortic valve placement: A feasibility study with a newly designed collapsible aortic valve," ASAIO Journal, Sep./ Oct. 1996, 42(5):M381-M385.

Nader Moazami et al., "Transliminal Aortic Valve Placement: A Feasibility Study With a Newly Designed Collapsible Aortic Valve," ASAIO Journal, Sep./Oct. 1996, Issue 5, vol. 42, pp. M381-M385.

Office Action for Australian Patent Application No. 2010328106, dated Jan. 2, 2014.

Office Action for Australian Patent Application No. 2010328106, dated Jun. 4, 2015.

Office Action for Australian Patent Application No. 2010328106, dated Sep. 8, 2015.

Office Action for Australian Patent Application No. 2012299311, dated Mar. 2, 2015.

Office Action for Canadian Patent Application No. 2,844,746, dated Apr. 28, 2015.

Office Action for Japanese Patent Application No. 2012-543269, dated Sep. 9, 2014.

Office Action for Japanese Patent Application No. 2012/543269, dated Jun. 30, 2015.

Office Action for U.S. Appl. No. 11/920,365, dated Apr. 4, 2014.
Office Action for U.S. Appl. No. 11/920,365, dated Aug. 3, 2009.
Office Action for U.S. Appl. No. 11/920,365, dated Feb. 26, 2010.
Office Action for U.S. Appl. No. 11/920,365, dated Feb. 28, 2011.
Office Action for U.S. Appl. No. 11/920,365, dated Mar. 14, 2012.
Office Action for U.S. Appl. No. 11/920,365, dated Oct. 2, 2012.
Office Action for U.S. Appl. No. 11/920,365, dated Sep. 17, 2013.
Office Action for U.S. Appl. No. 11/920,365, dated Sep. 23, 2010.
Office Action for U.S. Appl. No. 12/113,418, dated Aug. 28, 2012.
Office Action for U.S. Appl. No. 12/113,418, dated Feb. 2, 2012.
Office Action for U.S. Appl. No. 12/113,418, dated May 11, 2010.
Office Action for U.S. Appl. No. 12/113,418, dated Oct. 9, 2009.
Office Action for U.S. Appl. No. 12/677,958, dated Nov. 7, 2013, 5 pages.
Office Action for U.S. Appl. No. 12/691,591, dated Jan. 27, 2012.
Office Action for U.S. Appl. No. 12/959,292, dated Dec. 10, 2012.
Office Action for U.S. Appl. No. 12/963,596, dated Jul. 17, 2013.
Office Action for U.S. Appl. No. 12/963,596, dated Jul. 29, 2014.
Office Action for U.S. Appl. No. 13/141,498, dated Apr. 24, 2013.
Office Action for U.S. Appl. No. 13/141,498, dated May 29, 2014.
Office Action for U.S. Appl. No. 13/141,498, dated Oct. 16, 2012.
Office Action for U.S. Appl. No. 13/148,193, dated Apr. 11, 2013.
Office Action for U.S. Appl. No. 13/148,193, dated Feb. 13, 2014.
Office Action for U.S. Appl. No. 13/350,310, dated Mar. 5, 2014.
Office Action for U.S. Appl. No. 13/350,310, dated Nov. 28, 2014.
Office Action for U.S. Appl. No. 13/356,136, dated Feb. 28, 2014.
Office Action for U.S. Appl. No. 13/425,712, dated Apr. 22, 2014.
Office Action for U.S. Appl. No. 13/425,712, dated Aug. 16, 2013.
Office Action for U.S. Appl. No. 13/425,712, dated Jun. 18, 2015, 13 pages.
Office Action for U.S. Appl. No. 13/660,875, dated Aug. 28, 2014.
Office Action for U.S. Appl. No. 13/660,875, dated Jan. 2, 2014.
Office Action for U.S. Appl. No. 13/715,234, dated Mar. 13, 2015.
Office Action for U.S. Appl. No. 14/224,764, dated Jul. 31, 2015.
Office Action for U.S. Appl. No. 14/255,687, dated Nov. 3, 2015.

"Shape Memory Alloys," Retrieved from the Internet: <http://webdocs.cs.ualberta.ca/.about.database/MEMS/sma.html>, Nov. 14, 2012, 3 pages.

Al Zaibag, Muayed, et al., "Percutaneous Balloon Valvotomy in Tricuspid Stenos's," British Heart Journal, Jan. 1987, vol. 57, No. 1, pp. 51-53.

Al-Khaja, N. et al., "Eleven Years' Experience with Carpentier-Edwards Biological Valves in Relation to Survival and Complications," European Journal of Cardiothoracic Surgery, Jun. 30, 1989, 3:305-311.

Almagor, Y. et al., "Balloon Expandable Stent Implantation in Stenotic Right Heart Valved Conduits," Journal of the American College of Cardiology, Nov. 1, 1990, 16(6):1310-1314.

Andersen, H. R., "History of Percutaneous Aortic Valve Prosthesis," Herz, Aug. 2009, 34(5):343-346.

(56) References Cited

OTHER PUBLICATIONS

Andersen, H. R., "Transluminal catheter implanted prosthetic heart valves," International Journal of Angiology, 1998, 7(2): 102-106.
Benchimol, A. et al., "Simultaneous Left Ventricular Echocardiography and Aortic Blood Velocity During Rapid Right Ventricular Pacing in Man," The American Journal of the Medical Sciences, Jan.-Feb. 1977, 273(1):55-62.
Boudjemline, Y. et al., "Steps Toward the Percutaneous Replacement of Atrioventricular Valves: An Experimental Study," Journal of the American College of Cardiology, Jul. 2005, 46(2):360-365.
Buckberg, G. et al., "Restoring Papillary Muscle Dimensions During Restoration in Dilated Hearts," Interactive Cardiovascular and Thoracic Surgery, 2005, 4:475-477.
C. Orton, "Mitralseal: Hybrid Transcatheter Mitral Valve Replacement," www.acvs.org/symposium/proceedings2011/data/papers/102.pdf, pp. 311, 312.
Chamberlain, G., "Ceramics Replace Body Parts," Design News, Jun. 9, 1997, Issue 11, vol. 52, 5 pages.
Choo, S. J. et al., "Aortic Root Geometry: Pattern of Differences Between Leaflets and Sinuses of Valsava," The Journal of Heart Valve Disease, Jul. 1999, 8:407-415.
Curriculum Vitae of Robert A. Ersek, M.D., FACS, Jul. 10, 2009, http://www.ersek.com/rae-cv.htm.
Declaration of Malcolm J. R. Dalrymple-Hay, Nov. 9, 2012, pp. 1-11; with Curriculum Vitae, Oct. 4, 2012.
Dotter, C. T. et al., "Transluminal Treatment of Arteriosclerotic Obstruction. Description of a New Technic and a Preliminary Report of its Application," Circulation, Nov. 1964, 30:654-670.
Drawbaugh, K., "Feature—Heart Surgeons Explore Minimally Invasive Methods," Reuters Limited, Jul. 16, 1996, 3 pages.
Ellis Greenhalgh et al., "Design and Characterization of a Biometric Prosthetic Aortic Heart Valve," North Carolina State University. 1994, p. 137.
G. M. Bernacca, et al., "Polyurethane Heart Valves: Fatigue Failure, Calcification, and Polyurethane Structure," Journal of Biomedical Materials Research, Mar. 5, 1997, Issue 3, vol. 34, pp. 371-379.
Gray, H., Anatomy of the Human Body, 1947, pp. 474-479, 497-498.
Gray, H., The Aorta, Anatomy of the Human Body, 1918, Retrieved from the Internet <http://www.bartleby.com/107/142.html>, Dec. 10, 2012, 5 pages.
Gray, H., The Heart, Anatomy of the Human Body, 1918, Retrieved from the Internet <http://education.yahoo.com/reference/gray/subjects/subject/138>, Aug. 10, 2012, 9 pages.
Greenhalgh, E. S., "Design and characterization of a biomimetic prosthetic aortic heart valve," 1994, ProQuest Dissertations and Theses, Department of Fiber and Polymer Science, North Carolina State University at Raleigh, 159 pages.
H. R. Andersen et al., "Transluminal Implantation of Artificial Heart Valves: Description of a New Expandable Aortic Valve and Initial Results with Implantation by Catheter Technique in Closed Chest Pigs," European Heart Journal, 1992, Issue 5, vol. 13, pp. 704-708.
Inoue, K. et al., "Clinical Application of Transvenous Mitral Commissurotomy by a New Balloon Catheter," The Journal of Thoracic and Cardiovascular Surgery, 1984, 87:394-402.
International Preliminary Report on Patentability and Written Opinion for International Application No. PCT/US2006/019496, dated Dec. 11, 2007.
International Preliminary Report on Patentability for International Application No. PCT/US2012/072282, dated Jul. 8, 2014.
International Search Report and Written Opinion for International Application No. PCT/DE2008/001515, dated Dec. 10, 2008, 8 pages.
International Search Report and Written Opinion for International Application No. PCT/DE2009/000176, dated Oct. 20, 2009.
International Search Report and Written Opinion for International Application No. PCT/IB2014/060821, dated Oct. 10, 2014.
International Search Report and Written Opinion for International Application No. PCT/US2010/021686, dated Sep. 3, 2010.
International Search Report and Written Opinion for International Application No. PCT/US2010/023968, dated Oct. 19, 2010.
International Search Report and Written Opinion for International Application No. PCT/US2010/059582, dated Aug. 25, 2011.
International Search Report and Written Opinion for International Application No. PCT/US2012/050740, dated Mar. 29, 2013.
International Search Report and Written Opinion for International Application No. PCT/US2012/072282, dated Apr. 29, 2013.
International Search Report and Written Opinion for International Application No. PCT/US2013/051308, dated Nov. 8, 2013.
International Search Report and Written Opinion for International Application No. PCT/US2014/040188, dated Nov. 17, 2014.
International Search Report and Written Opinion for International Application No. PCT/US2014/044047, dated Nov. 17, 2014.
International Search Report and Written Opinion for International Application No. PCT/US2014/049218, dated Oct. 20, 2014.
International Search Report and Written Opinion for International Application No. PCT/US2014/058826, dated Jan. 20, 2015, 14 pages.
International Search Report and Written Opinion for International Application No. PCT/US2015/019418, dated Sep. 10, 2015, 16 pages.
International Search Report and Written Opinion from corresponding International Patent Application PCT/US2012/050579, dated Feb. 26, 2013.
International Search Report for International Application No. PCT/US2006/019496, dated Dec. 18, 2006.
International Search Report for International Application No. PCT/US2014/061046, dated Feb. 24, 2015.
International Search Report from International Application No. PCT/US2009/041754 dated Sep. 25, 2009.
International Search Report from International Application No. PCT/US2009/041754 dated Dec. 8, 2009.
International Search Report from International Application No. PCT/US2010/058860 dated Aug. 25, 2011.
Invitation to Pay Additional Fees and Partial International Search Report for International Application No. PCT/US2014/040188, dated Sep. 8, 2014.
Invitation to Pay Additional Fees and Partial International Search Report for International Application No. PCT/US2014/044047, dated Sep. 8, 2014.
Jin, X. Y. et al., "Aortic Root Geometry and Stentless Porcine Valve Competence," Seminars in Thoracic and Cardiovascular Surgery, Oct. 1999, 11(4)1145-150.
Kevin Drawbaugh, "Feature—Heart Surgeons Explore Minimally Invasive Methods," Reuters, Jul. 16, 1996.
Office Action for U.S. Appl. No. 14/322,294, dated Sep. 28, 2015.
Office Action for U.S. Appl. No. 12/677,958, dated Jun. 20, 2012, 5 pages.
Office Action for U.S. Appl. No. 13/275,683, dated Apr. 11, 2013, 6 pages.
Office Action for U.S. Appl. No. 13/275,683, dated Mar. 1, 2012, 7 pages.
Office Action for U.S. Appl. No. 13/275,751, dated Mar. 30, 2012, 7 pages.
Office Action for U.S. Appl. No. 13/464,367, dated Apr. 23, 2014, 5 pages.
Office Action for U.S. Appl. No. 13/464,367, dated Jun. 17, 2013, 4 pages.
Office Action for U.S. Appl. No. 14/465,437, dated Jan. 16, 2015, 5 pages.
Orton, C., "Mitralseal: Hybrid Transcatheter Mitral Valve Replacement," Symposium: Small Animal Proceedings, 2011, pp. 311-312.
Pavcnik, M.D., Ph.D., Dusan, et al. "Development and Initial Experimental Evaluation of a Prosthetic Aortic Valve for Transcatheter Placement," Cardiovascular Radiology 1992; 183:151-154.
Porstmann, W et al., "Der Verschluß des Ductus Arteriosus Persistens ohne Thorakotomie," Thoraxchirurgie Vaskuläre Chirurgie, Band 15, Heft 2, Stuttgart, Apr. 1967, pp. 199-203.
Rashkind, W. J., "Creation of an Atrial Septal Defect Without Thoracotomy," The Journal of the American Medical Association, Jun. 13, 1966, 196( 11 ): 173-174.

(56) References Cited

OTHER PUBLICATIONS

Rashkind, W. J., "Historical Aspects of Interventional Cardiology: Past, Present, Future," Texas Heart Institute Journal, Dec. 1986, 13(4):363-367.
Reul, H. et al., "The Geomety of the Aortic Root in Health, at Valve Disease and After Valve Replacement," J. Biomechanics, 1990, 23(2):181-191.
Robert C. Ashton Jr., "Development of an Intraluminal Device for the Treatment of Aortic Regurgitation: Prototype and in Vitro Testing System," Journal of Thoracic and Cardiovascular Surgery, 1996, Issue/vol. 112, pp. 979-983.
Rosch, J et al., "The Birth, Early Years and Future of Interventional Radiology," J Vase Interv Radiol., Jul. 2003, 4:841-853.
Ross, D. N., "Aortic Valve Surgery," Guys Hospital, London, 1968, pp. 192-197.
Rousseau, E. P. M. et al., "A Mechanical Analysis of the Closed Hancock Heart Valve Prosthesis," Journal of Biomechanics, 1998, 21(7):545-562.
Sabbah, A. N. et al., "Mechanical Factors in the Degeneration of Porcine Bioprosthetic Valves: An Overview," Dec. 1989, Journal of Cardiac Surgery, 4(4):302-309.
Selby, M.D., J. Bayne, "Experience with New Retrieval Forceps for Foreign Body Removal in the Vascular, Urinary, and Biliary Systems," Radiology 1990; 176:535-538.
Serruys, P.W., et al., "Stenting of Coronary Arteries. Are we the Sorcerer's Apprentice?," European Heart Journal (1989) 10, 774-782, pp. 37-45, Jun. 13, 1989.
Shape Memory Alloys, ttp://webdocs.cs.ualberta.ca/.about. database; Nov. 14, 2012, pp. 1-3.
Sigwart, U., "An Overview of Intravascular Stents: Old and New," Chapter 48, Interventional Cardiology, 2nd Edition, W.B. Saunders Company, Philadelphia, PA, © 1994,1990, pp. 803-815.
Supplementary European Search Report for European Application No. 10738954.6, dated May 9, 2014.
Supplementary European Search Report for European Application No. 10835174.3, dated Jun. 11, 2014.
Supplementary European Search Report for European Application No. 12825480.2, dated Jul. 31, 2015.
Supplementary Search Report for European Application No. 10836657.6, dated Jan. 5, 2015.
Tofeig, M et al., "Transcatheter Closure of a Mid-Muscular Ventricular Septal Defect with an Amplatzer VSD Occluder Device," Heart, 1999, 81:438-440.
U.S. Appl. No. 09/975,750, filed Oct. 11, 2001, Spenser et al.
U.S. Appl. No. 13/350,310, filed Jan. 13, 2012, Rowe.
U.S. Appl. No. 13/356,136, filed Jan. 23, 2012, Chau et al.
U.S. Appl. No. 60/635,275, filed Dec. 9, 2004, Gifford et al.
U.S. Appl. No. 60/662,764, filed Mar. 16, 2005, Gifford et al.
U.S. Appl. No. 60/698,297, filed Jul. 11, 2005, Gifford et al.
Uchida, Barry T., et al., "Modifications of Giantulco Expandable Wire Stents," AJR:150, May 1988, Dec. 3, 1987, pp. 1185-1187.
Urban. P., "Coronary Artery Stenting," Editions Medecine et Hygiaene, Genaeve, 1991, pp. 5-47.
US 9,155,620, Oct. 2015, Gross et al. (withdrawn).
Watt, A.H., et al. "Intravenous Adenosine in the Treatment of Supraventricular Tachycardia; a Dose-Ranging Study and Interaction with Dipyridamole," British Journal of Clinical Pharmacology (1986), 21, pp. 227-230.
Webb, J. G et al., "Percutaneous Aortic Valve Implantation Retrograde from the Femoral Artery," Circulation, 2006, 113:842-850.
Wheatley, M.D., David J., "Valve Prostheses," Rob & Smith's Operative Surgery, Fourth Edition, pp. 415-424, ButtenNorths 1986.
Yoganathan, A. P. et al., "The Current Status of Prosthetic Heart Valves," In Polymetric Materials and Artificial Organs, Mar. 20, 1983, pp. 111-150, American Chemical Society.

* cited by examiner

TRUNCATED CONE HEART VALVE STENT

CROSS-REFERENCE TO RELATED APPLICATIONS

This application is a continuation of U.S. patent application Ser. No. 15/653,653, filed Jul. 19, 2017, which is a continuation of U.S. patent application Ser. No. 15/018,473, filed Feb. 8, 2016, now U.S. Pat. No. 9,730,792, which is a continuation of U.S. patent application Ser. No. 14/746,381, filed Jun. 22, 2015, now U.S. Pat. No. 9,254,192, which is a divisional of U.S. patent application Ser. No. 14/465,437, filed Aug. 21, 2014, now U.S. Pat. No. 9,078,749, which is a continuation of U.S. patent application Ser. No. 13/275,683, filed Oct. 18, 2011, now U.S. Pat. No. 9,095,433, which is a continuation of U.S. patent application Ser. No. 12/677,958, filed Sep. 9, 2010, which claims priority under 35 U.S.C. § 371 to, and is a U.S. national phase entry of, International Application No. PCT/DE2008/001515, filed Sep. 10, 2008, which claims priority to German Application No. 10 2007 043 830.5, filed Sep. 13, 2007. The disclosure of each of the foregoing applications is incorporated herein by reference in its entirety.

BACKGROUND

Field of the Invention

The invention refers to a valve stent with a section equipped to receive a heart valve implant and several of proximally disposed anchoring elements.

Such heart valve stents are known in various forms for the replacement dysplastic and degenerated heart valves. Thereby, the surgical implantation of heart valve prostheses is regularly accomplished in the cardioplegic heart. The old, functionally degenerated heart valve is resected and the new, implantable heart valve is sewed in.

However, when the mitral valve is affected, one tries, as far as possible, to maintain the old valve in spite of its malfunctioning so that the entire dynamic mitral valve apparatus is not disturbed. The reason for this is that, for instance, the chordae tendineae, which are attached to the mitral valve are very important for ventricular function. Therefore, they should preferably not be removed from the old mitral valve.

Ideally, the mitral valve (in case the old valve cannot be reconstructed) will be pushed aside as far as possible to make room for a new valve. Space does not play such an important role as compared to the aortic annulus which can be more easily stenosed (i.e., during displacement of the old aortic valve for sole percutaneous implantation).

The chordae tendineae of the mitral valve shall be, if possible, structurally maintained to preserve the ventricular geometry and hence of the left ventricle or achieve optimal function of the left chamber as far as possible. Therefore, a best possible function of the left chamber is obtained and achieved. Of significant relevance is that the anterior mitral valve leaflet is not pushed aside into the free space toward the left ventricle, but rather that it is attached to the mitral annulus so that a press forward of the anterior leaflet into the left ventricular outflow tract (LVOT) is avoided ("sam" phenomenon: systolic anterior movement). This is extremely important, because otherwise a left heart decompensation (massive dysfunction of the left ventricle) could rapidly occur.

Surgically the old mitral valve is attached to the old annulus so that there is a free flow of blood through the valve and both adjacent heart chambers. After pushing aside (attachment of the valve onto the annulus) the heart valve prosthesis is surgically implanted into the annulus.

This extensive method mandatorily takes place with the help of a heart- and lung-machine. For high risk patients it is usually not used and minimally invasive and percutaneous methods to perform the implantation of a heart valve are sought.

In this context, the German patent DE 195 46 692 C2 and the corresponding EP 1 469 797 B1 is known. This patent describes a self-expanding heart valve prosthesis for the implantation into a human body using a catheter system with a heart valve and a foldable, valve-connected and expanding stent. Such a self-expanding heart valve prosthesis can be directed through the femoral artery with the help of a catheter based system to the area of cardiac implantation. After the stent reaches the area of implantation, it can be successively unfolded. Along its long axis, the stent is composed of several, at angles to each other, self-expanding segments that are unfolded gradually. After expansion, the heart valve prosthesis can be anchored with the support of hooks at least in the respective blood vessel close to the heart.

Another apparatus for the fixation and anchorage of heart valve prostheses is described in the German Patent 100 10 074 A1 which fundamentally consists of wire-like elements attached together. Different brackets are hereby used to secure anchorage and brace a heart valve.

Even with the known solutions there is still the danger that a heart valve will be incorrectly implanted due to wrong positioning and deficient angular adjustment of the heart valve prosthesis.

Improved positioning and angular alignment for the aortic valve can be reached by the stent described in the European Patent EP 1 469 797 B1 which consists of supportive holders which can be inserted into the aortic pouches and create a defined distance to the aortic valve. Beyond this, the possibility exists to halt a failed implantation of a heart valve prosthesis and to push the valved stent ("a valve integrated into a stent") back into the catheter delivery system (more precisely the "cartridge"). Thereby, it is possible that the stent can again slide out when good positioning for the valved stent has been reached. Thus, the valved stent can be taken in and out until the optimal positioning has been achieved ("sliding technique").

A much larger problem for the optimal positioning of the new heart valve in the stent (alternatively valved stent) still exists in the following: in most cases the old, native valve will not be eliminated by the above-described technique of implantation.

This leads to the fact that the new valve which will be pressed into (partly squashed into) the old, deformed valve will be transformed into the original form. The reason for this is that the location of implantation for the valved stent is affected by the morphology, the shape and consistency of the old native valve (for instance by sclerosis or calcification of the native valve).

Therefore, the old annulus of the valve with the corresponding changed valves pouches determines to what extent and where the native valve will unfold and whether its form can develop. Hence, for the optimal function of the valve and maintenance of the atrial and ventricular function not only the anchorage/positioning is important, but also the fitting of the valve stent into the neo-annulus (old valve annulus with old valve shapes it) and with it the pushing back of the old valve.

Based on the fact that there are known problems of the valved stents, the challenge of this intervention is to produce a heart valved stent, especially a mitral valved stent, for minimally-invasive transplantation, which preferably facilitates the natural functioning of the heart.

SUMMARY

Referring to the invention, this problem will be solved with the heart valved stent and its features from claim 1. The subclaims provide advantageous designs for setting up the intervention.

The basic idea of the invention is to produce a heart valve stent which establishes the anatomic requirements for the natural exertion of the function—like a healthy heart. In the process, the invention-related heart valve stent with its self-expanding, foldable embodiment establishes a minimally-invasive operation which assures an exact positioning and secure fixation of the valve stent. Thereby, a tension between the mitral valve and ventricle similar to the natural tension of the chordae tendineae is generated, and at the same time it will be provided that the valve parts of the old mitral valve (especially the anterior mitral valve leaflet) will not disturb the flow rate of the blood.

Therefore, it is intended that the valve stent, according to the invention, is catheter-inserted into one of the heart chambers or into the adjacent large vessels of the heart, then unfolded in one of the heart chambers, whereupon its anchoring elements are fixed in the tissue. Finally, the stent is fixed at its opposed, subvalvular wall of the heart chamber under development of a tension between the wall of the heart chamber and the proximal, supravalvular, fixed anchoring elements with anchoring sutures (hereafter referred to as neo-chordae).

The fixation of the anchoring sutures in the distal wall of the heart chamber exhibits a thrust bearing to the proximal anchoring elements which will be established by a joint or another element acting as a thrust bearing. This counter bearing can be preferentially designed also as an adjusting element for the length of the sutures.

Advantages of the heart valve stents which according to the intervention are the exact and easy fixation of the heart valve stent and improved contractility of the heart in minimally invasive operations in comparison with customary valve stents.

Preferentially, the axially, relatively to the longitudinal axis, arranged anchoring sutures are fixed according to the invention (the valve stent) with one end to the annulus of the heart valve implant, so that after development of a tension between the stent and the wall of the ventricle, the positioning and the angular arrangement of the valve can be directly impacted. The anchoring sutures can also be fixed at the distal part of the circumference of the valve stent. The connection between the anchoring sutures and the stent has to be conducted so that a tension which should run fundamentally in an axial direction relative to the long axis of the stent and is formed between the proximal anchoring elements and the distal counter bearing.

According to another preferential design of the invention, the anchoring sutures (neo-chordae) have elements to adjust the length of the anchoring sutures so that through the length of the anchoring sutures a certain tension between the heart valve stent and the heart wall can be regulated.

Thereby, an adjusting element, for example, for the individual length of sutures or for all sutures together can be allowed for. The adjusting element for the length of sutures is preferably designed small and can, for instance, be constructed in such a manner that this element shortens the suture to the desired length by rolling up the excess thread.

The construction of the elastic anchoring sutures along the axis are also preferred so that they are able to react to heart contractions without having too sutures that might negatively affect the heart function. Here the suture length should be selected so that the elasticity is not sacrificed due to the tension between the anchoring elements and the heart wall.

After adjusting the counter bearing of the adjusting element to the length of sutures, a notably beneficial design is made so that also a re-adjustment of the tension between the anchoring elements and the counter bearing, i.e. a re-tensioning of the anchoring sutures is possible without opening the heart.

Especially favored is the structure of the mitral valve stent which is fundamentally oval or u-shaped in the plane of the mitral valve annulus so that no pressure to the LVOT (left ventricular outflow tract) and/or aortic annulus is exerted. Therewith damage to the hearts function is stopped (Ma L, Tozzi P, Huber C H, Taub S, Gerelle G, von Segesser L K. Double-crowned valved stents for off-pump mitral valve replacement. Eur J Cardiothorac Surg. 2005 August; 28 (2):194-8; discussion 198-9). Additionally, the subvalvular apparatus also completely retains its natural anatomy and is not compromised (Boudjemline Y, Agnoletti G, Bonnet D, Behr L, Borenstein N, Sidi D, Bonhoeffer P. Steps toward the percutaneous replacement of atrioventricular valves, an experimental study. J Am Coll Cardiol. 2005 Jul. 19; 46 (2) i360-5).

This valve stent has for the natural mitral valve apparatus a completely adapted, exceedingly nestled form so that this conically tapered (cranial-caudal axis) not entirely circular (oval-like in the transversal axis) valve stent is able to attach to and abut to the natural form of the mitral valve. In the area of the anterior mitral valve annulus, the valve stent is flat and exerts almost no pressure on and does not constrict the LVOT. In the area of the posterior mitral valve annulus, it is oval and replicates a form like the posterior annulus. This valve stent forms a thin, restricted along the length (cranial-caudal) structure which in its form aligns completely to the mitral valve and thus in the area of the natural mitral valve annulus looks like a negative impression of it. In fact, the valve stent contacts the old mitral valve and the annulus, but leaves their anatomy completely unchanged.

BRIEF DESCRIPTION OF THE DRAWINGS

In the following the invention will be closely elucidated by means of the attached figures representing the particularly preferred execution examples. It shows.

DETAILED DESCRIPTION

Figure 3:
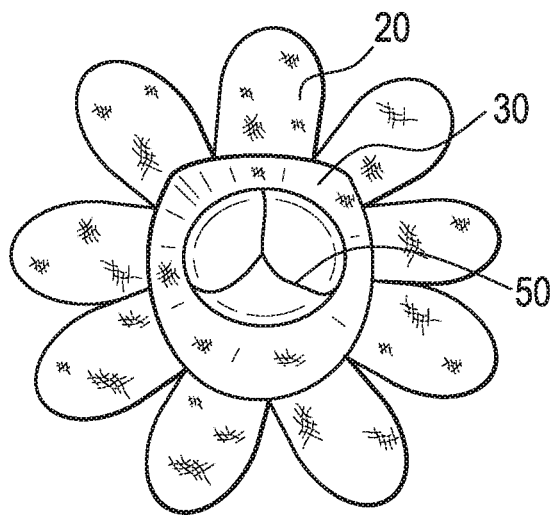
FIG. 3 top view on several especially preferred valve stents according to the invention.
Figure 3:
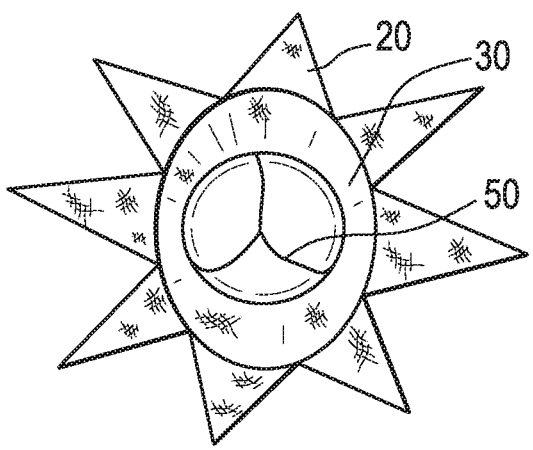
Figure 3:
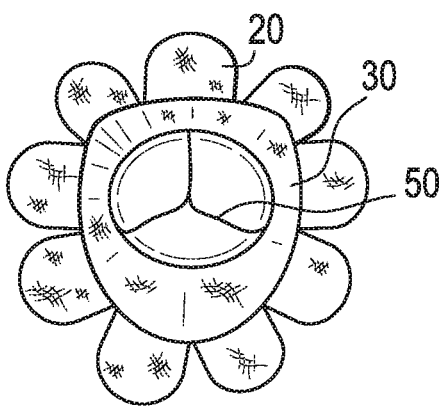
Figure 3:
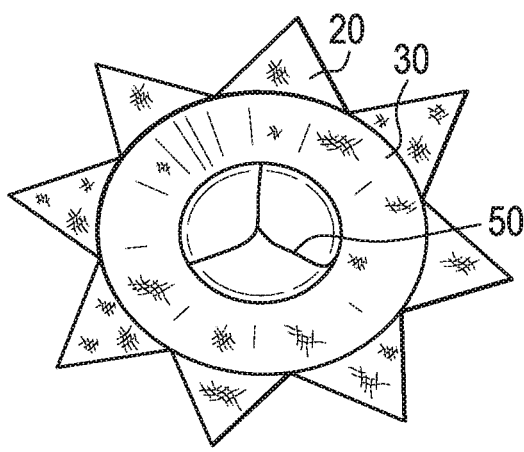
Figure 4:
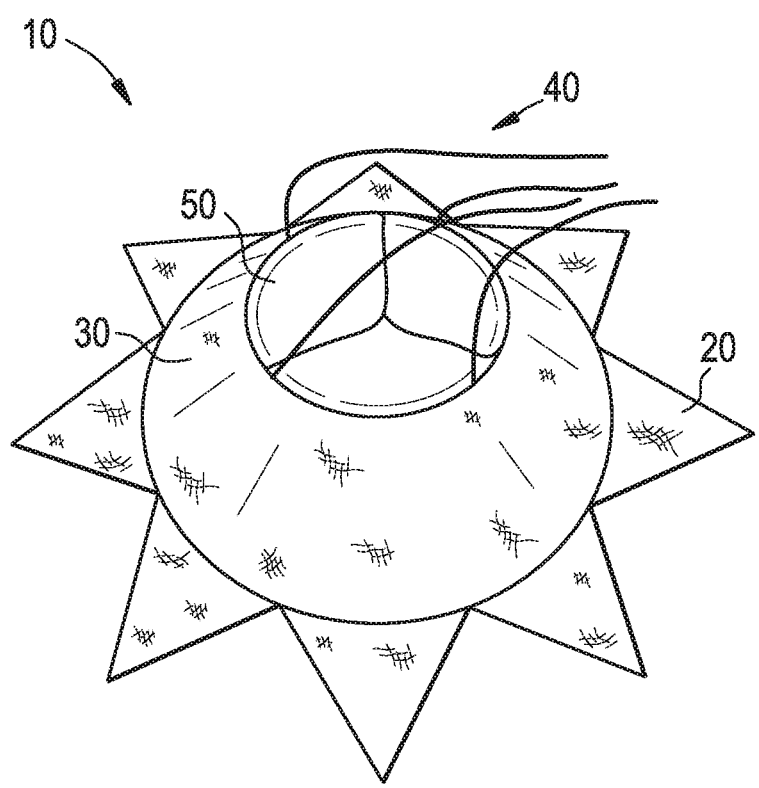
FIG. 4 a top view from an execution example from below.
Figure 5:
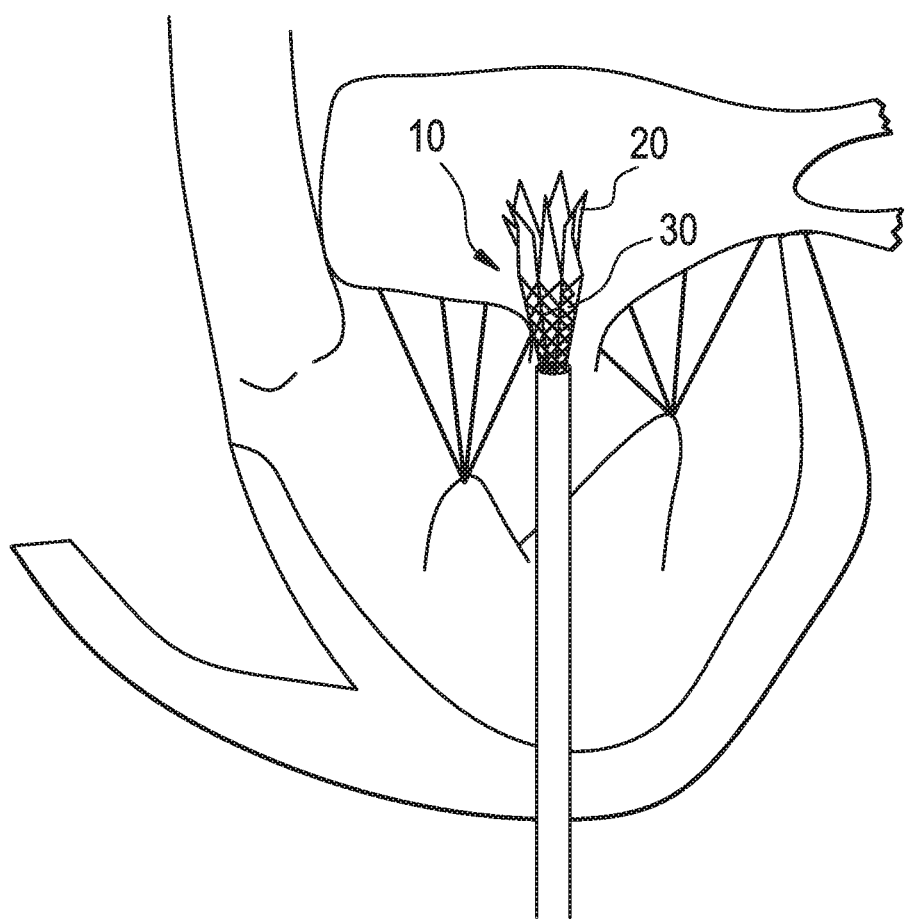
FIG. 5 a schematic view which explains the minimally-invasive transplantation of the mitral valve stent according to the invention in a first phase of insertion of the mitral valve stent into the location of transplantation.

The FIGS. 1 to 11 indicate the stent according to the invention for the implantation and fixation of heart valve prostheses in different views to show the configuration of the stents and the spatial relations of individual parts of the stent to each other in an unfolded (FIGS. 1-4 and 6-11) and in a folded condition (FIG. 5).

Figure 1:
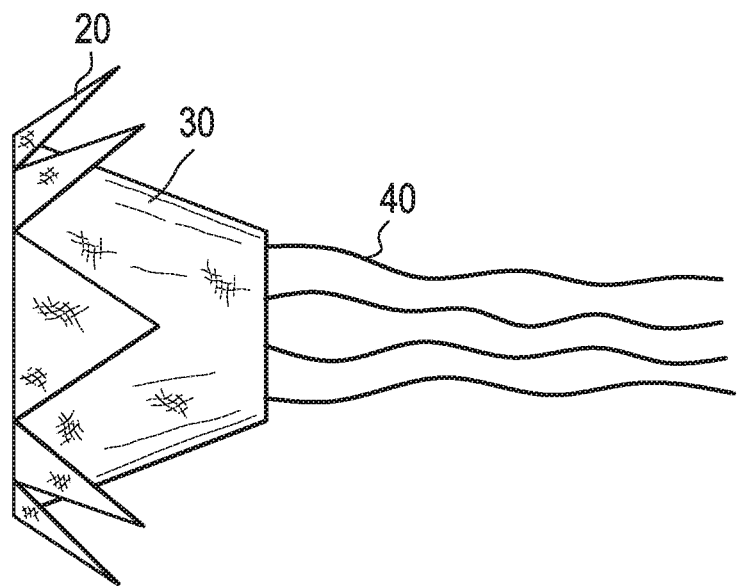
FIG. 1 a favored execution example of the valve stent according to the invention in a schematic lateral view.

FIG. 1 shows a foldable mitral valve stent 10 according to the invention in a perspective lateral view. The stent 1-0 exhibits mainly three parts: proximally (supravalvularly) on stent 10 there are several serrated, arched anchoring (FIG. 3) elements circularly arranged which are able to anchor supravalvularly (respectively atrially) the valve stent 10 in an implanted condition. The preferable stent body 30 flattened to the LVOT is distally adjoined and is conical and in cross section ovally shaped (compare FIG. 2).

The stent body 30 forms a basket- or trapezoid-like figure which nestles to the mitral valve annulus and extends in the direction of the left ventricle. This stent 10 is held in the atrium due to its conically-tapered form and due to the atrial anchoring elements 20. A bi- or tri-leaflet valve 50 can be integrated into the stent body 30.

At the distal part of the stent body 30 (to the direction of the left ventricle) there are anchoring sutures 40 which are distally equipped to the stent body 30 for the anchorage of the entire stent 10. These anchoring sutures 40 provide for an anchorage in the opposed wall of the ventricle or for instance in the area of the papillary muscles 30 (proximal, medial or distal part of the papillary muscle); compare FIGS. 7 and 8. With the help of a adjusting element to regulate the length of sutures 70, these anchoring sutures 40 can be positioned and adjusted to the optimal length so that the heart valved stent 10 can be fixed and anchored.

Figure 2:
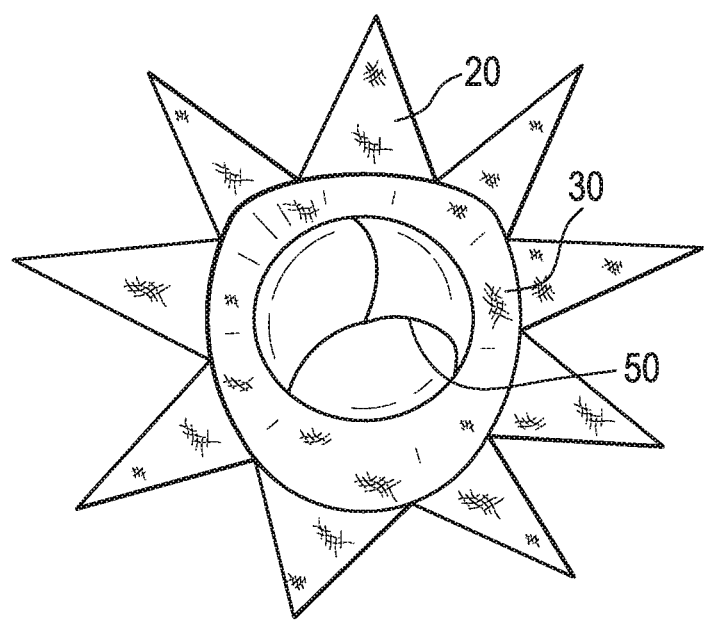
FIG. 2 the demonstrated execution example in FIG. 1 with top view from above.

FIG. 2 indicates the stent 10 in a top view. Thereby, it can be distinguished that stent 10 forms a neo-annulus, alternatively a stent body 30 in which the heart valve prosthesis 50 can be implanted and in which it can be fixed. Furthermore, it can be recognized that the invention-like stent 10 can be shaped asymmetrically in relation to several supravalvular (atrial) stent brackets 20.

This can be identified by the fact that the stent body 30 is oval-like and flattened on one side as seen in this figure, so it (the stent body 30) can be installed with its flattened side towards the direction of the LVOT. This flattening has the consequence that no pressure on this side towards the LVOT and towards the aortic valve can be exerted from the self-expanding stent in case the stent 10 is used, i.e. in the mitral position. Further favored embodiments of the stent 10 are indicated in FIG. 3 according to the invention.

FIG. 4 demonstrates the invention-pertaining stent 10 from a bottom view. From this it is obvious that the diameter of the atrial part to the ventricular part of the stent body 30 becomes smaller so that this looks like a truncated cone from the lateral view (compare FIG. 1). The anchoring elements 20 as well as the stent body 30 can be upholstered with cloth (i.e. synthetics, pericardium, PTFE or Goretex, etc.) to achieve better sealing between the heart valve prosthesis 50, stent body 30 and the surrounding heart structure. This sealing membrane is tapered/alternatively upholstered between the heart valve prosthesis 50, the stent body 30 or onto the atrial stent struts 20 to achieve optimal sealing of the valve between both heart chambers.

In FIGS. 5 to 7 and 8, the retrograde trans-apical implantation of the valved stent is described. The retrograde trans-aortic as well as the antegrade trans-atrial approach can stent above the old mitral annulus is shown in FIG. 5. A slow unfolding (preferred self-expanding) of the atrial anchoring elements 20 can be started after successful orientation with support of labeling at the valve stent 10 (not shown). The positioning in the left atrium should be done in that way that the flattened side of the stent body 5 is turned towards the direction of the LVOT (aortic valve). The stent will be further expanded.

Figure 6:
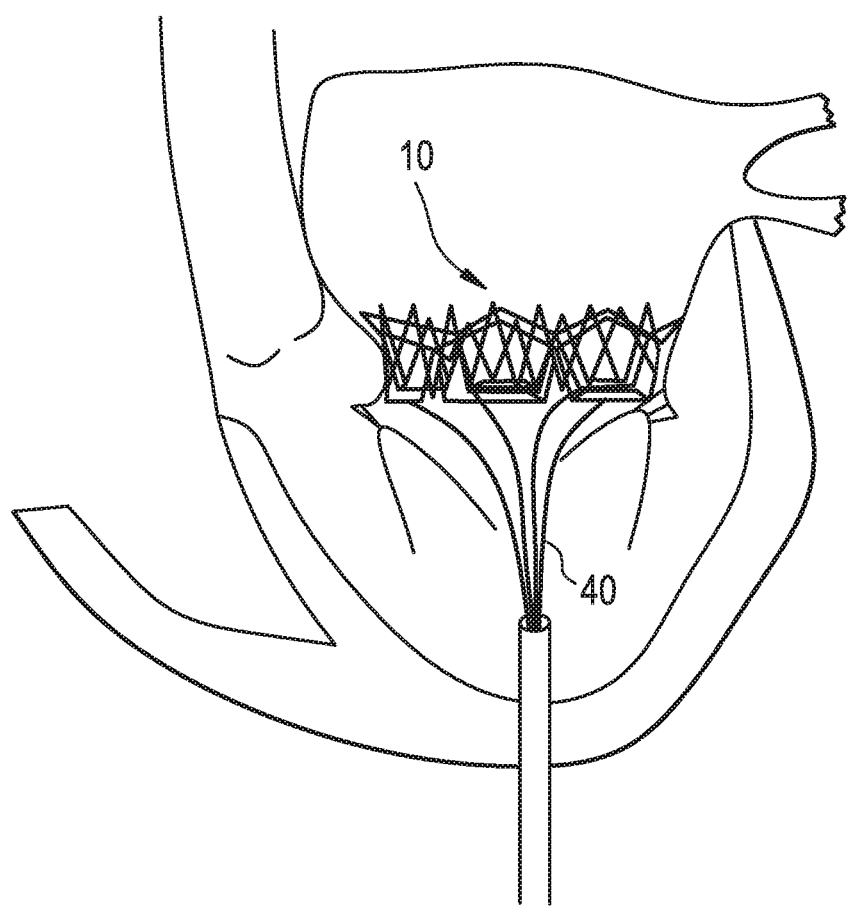
FIG. 6 a schematic view for the demonstration of the minimally-invasive transplantation of the mitral valve stents according to the invention in a second phase after positioning of the mitral valve.
Figure 7:
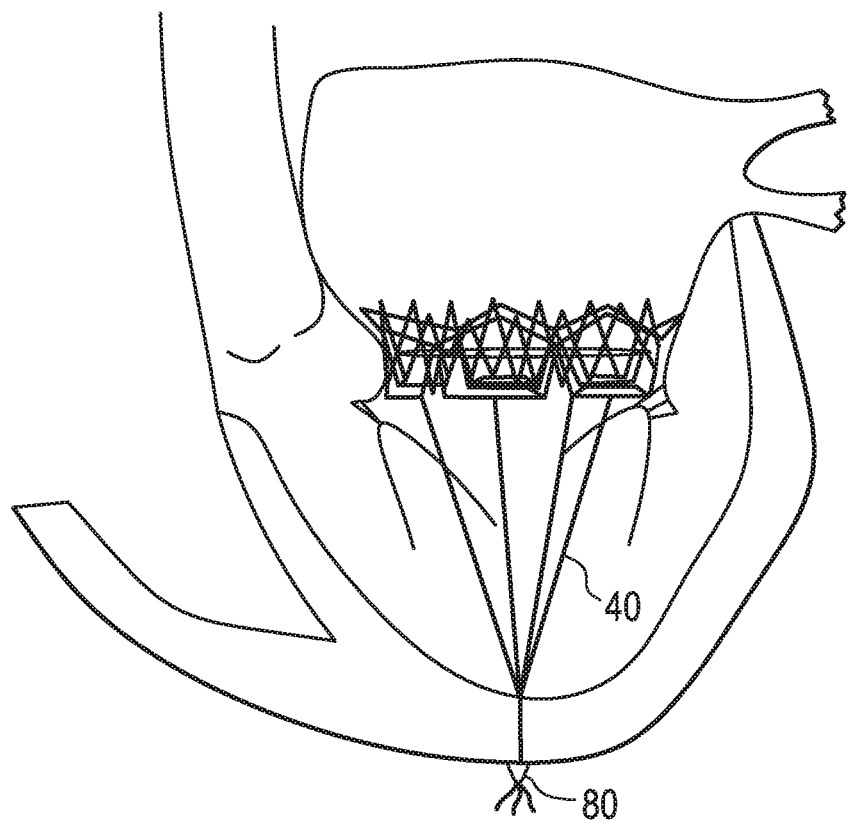
FIG. 7 a schematic view for demonstration of the minimally invasive transplantation of the mitral valve stent after completion of the fixation of the anchoring sutures outside of the apex of the ventricular heart wall.
Figure 8:
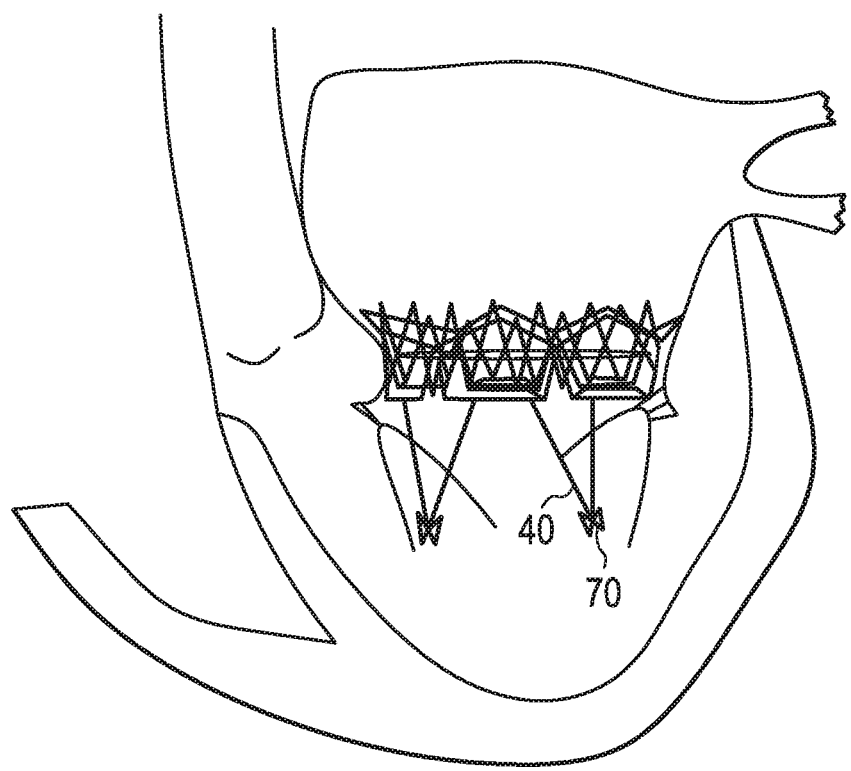
FIG. 8 a schematic view of an alternative, intra-cardiac fixation of the anchoring sutures in the area of papillary muscles.

FIG. 6 indicates the expanded valve stent 10 in the left-atrio-ventricular in-flow tract. Anchoring sutures 40 are adjusted in or outside the wall of the heart and later—as shown in FIG. 7—they will be fixed with the support of the thrust bearing 80 which is favorably designed as an adjusting element for the length of sutures. During the adjustments for the length of the anchoring sutures 40, visualization of the mitral valve apparatus (i.e. Echo, CT, NMR) is carried out so as to optimally pull the annulus of the new stent 10 toward the ventricular wall, paravalvular leakage no longer exists, the stent 10 can be fixed in a good manner, and the mitral valve annulus and apparatus support advantageously the left ventricular function.

Alternatively to FIG. 7, the anchoring sutures 40 can also be fixed at the papillary muscles (see FIG. 8) so that these sutures 40 represent the neo chordae and take 20 over the function of the functionless chordae tendineae. The fixation of the anchoring sutures 40 at the wall of the heart in each case result from a thrust bearing 80 which can be developed as a knot or also as an independent element. It is also possible that the ventricular anchoring sutures 40 are not only affixed to the stent body 30, but also at the integrated valve itself. The caudal anchoring sutures 40 can also be fixed at any other point of the ventricle.

FIG. 7 shows the accomplished positioning and fixation of the stent 10. After the length and location of the single anchoring sutures 40 has been determined, these anchoring sutures 40 will be fixed with the suture-length adjusting elements 70, for instance, in the left ventricular wall. The suture-length adjusting element 70 is used for the optimal calibration of the length and position of the valve stent 10 and therefore for the valve prosthesis 50. Different sutures 40 can exhibit different length and fixing positions in the ventricle.

Figure 9:
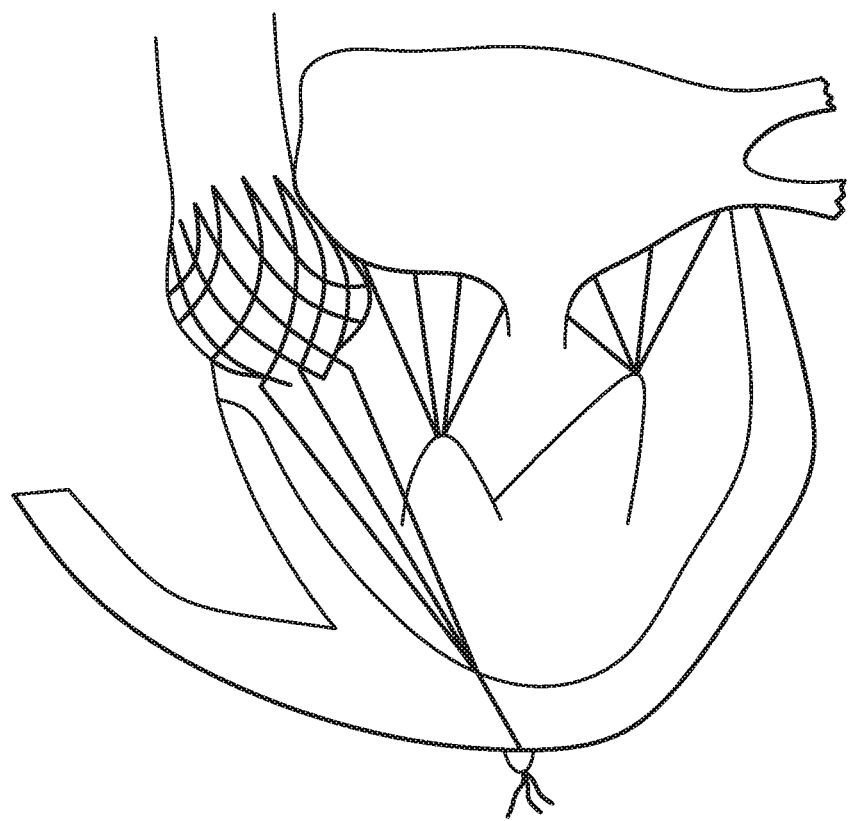
FIG. 9 a schematic view of a heart valve stent which is fixed in the aortic annulus according to the invention.
Figure 10:
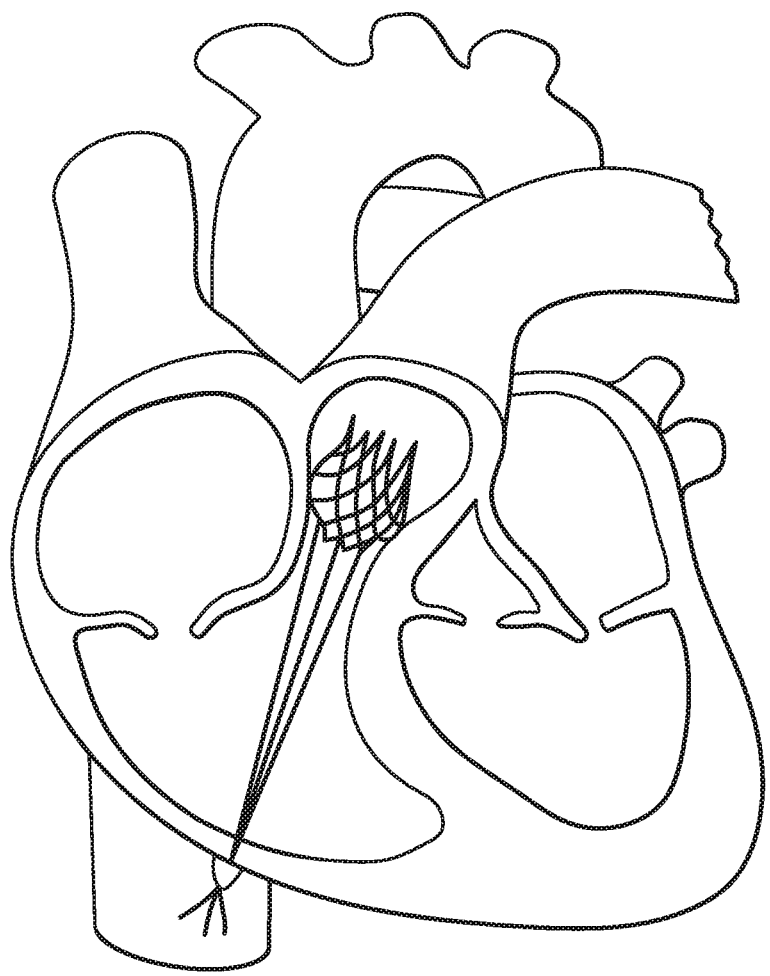
FIG. 10 a schematic view of a heart valve stent which is fixed in the pulmonary position according to the invention.
Figure 11:
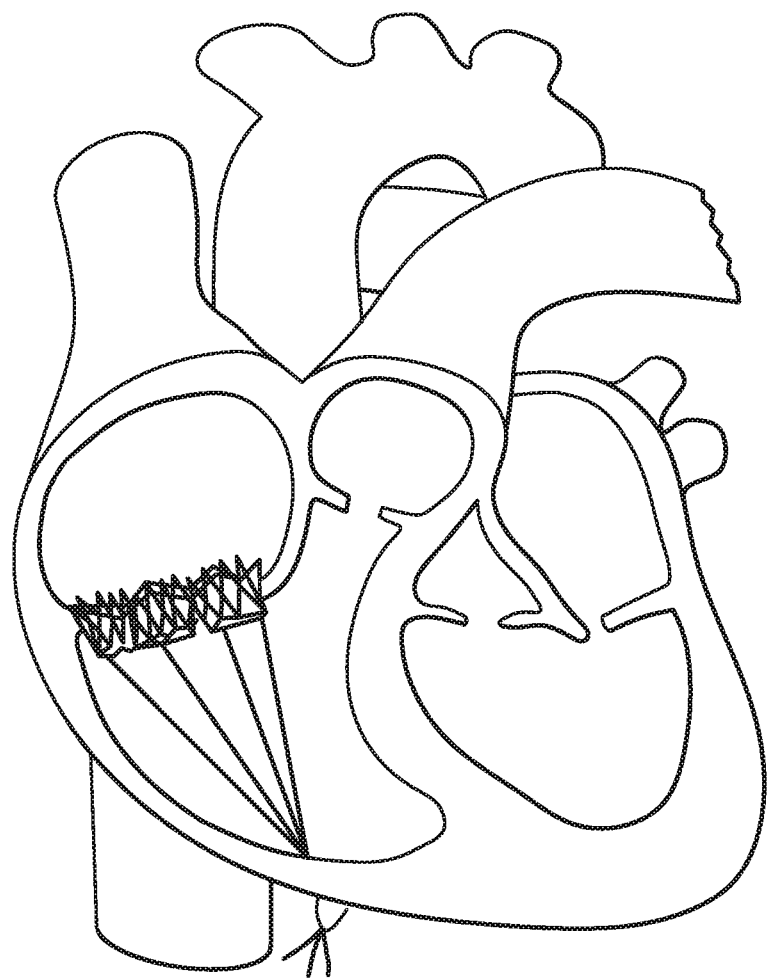
FIG. 11 a schematic view of a heart valve stent which is fixed in the tricuspid position according to the invention.

FIGS. 9 to 11 demonstrate additional examples for the application of the valve stent 10 according to the invention, whereas the stent 10 is readjusted to the particular anatomy (for the aortic- and pulmonary valve position a rather circular form (compare FIG. 3) and for the tricuspid position a rather oval form).

Figure 12:
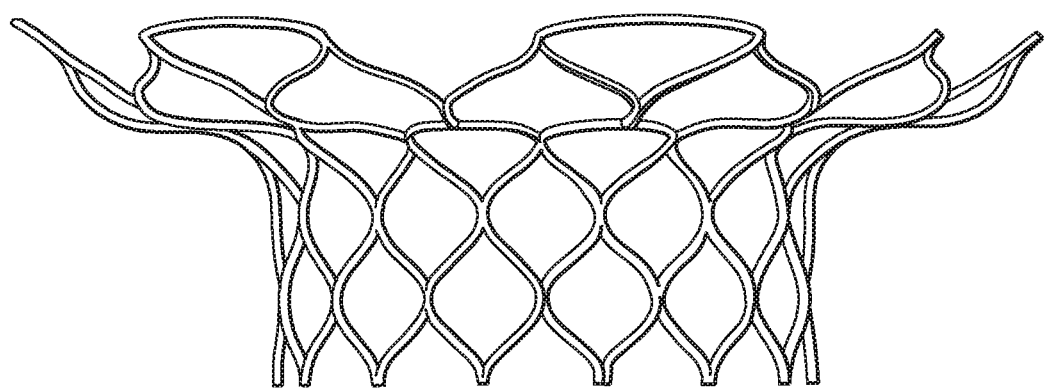
FIG. 12 an especially preferred execution example of the valve stent (according to the invention) in a schematic lateral view without heart valve and anchoring sutures.
Figure 13:
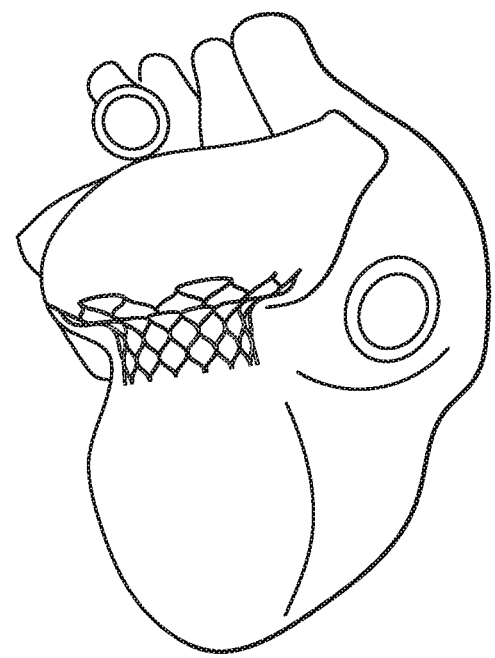
FIG. 13 a schematic dorsal, intra-cardiac view of a heart valve stent which is fixed in the mitral position according to the invention.

FIG. 12 shows an especially preferred designed execution example of the valve stent pertaining to the invention in a schematic lateral view which is shown without heart valve and anchoring sutures for a better clearness. For clarification in FIG. 12 of the positioning of the valve stent in situ, FIG. 13 demonstrates a schematic, dorsal, intra-cardiac view of a fixed heart valved stent in the mitral position according to the invention. Note the good alignment of the valved stent with the left atrial environment. Distances between the left atrial wall/mitral annulus and the valved stent are avoided. Heart valve and anchoring sutures for the ventricular apex have been omitted for simplification.

What is claimed is:

1. A prosthetic mitral valve comprising:
   a self-expanding stent having a proximal atrial section and a distal body section;
   a prosthetic valve assembly disposed within the body section of the stent; and
   a cloth member positioned on an exterior surface of the atrial section of the stent;
   wherein the atrial section of the stent includes a first tissue anchor connected to, and flaring radially outward from, a first end of the body section, the first tissue anchor including a plurality of circumferentially arranged expandable stent cells adapted to anchor to a first tissue area on an atrial side of a native mitral valve annulus;
   wherein the body section of the stent includes a plurality of second tissue anchors extending therefrom adapted to anchor to a second tissue area disposed distally to the first tissue area; and
   wherein the cloth member on the atrial section of the stent is adapted to directly contact surrounding heart structure to provide a seal between the atrial section of the stent and the surrounding heart structure.

2. The prosthetic mitral valve of claim 1, wherein the prosthetic valve assembly is directly coupled to the body section of the stent.

3. The prosthetic mitral valve of claim 1, wherein the cloth member is formed of a material selected from the group consisting of synthetics, pericardium, and polytetrafluoroethylene.

4. The prosthetic mitral valve of claim 1, wherein the cloth member is also positioned on an exterior surface of the body section of the stent.

5. The prosthetic mitral valve of claim 1, wherein the plurality of second tissue anchors includes a plurality of anchoring sutures.

6. The prosthetic mitral valve of claim 1, wherein the body section of the stent has a shape of a truncated cone.

7. The prosthetic mitral valve of claim 1, wherein one side of the body section is flattened relative to another side of the body section.

8. The prosthetic mitral valve of claim 1, wherein the plurality of second tissue anchors are attached to a second end of the body section opposite the first end.

9. The prosthetic mitral valve of claim 1, wherein the plurality of circumferentially arranged expandable stent cells are triangular-shaped.

10. The prosthetic mitral valve of claim 1, wherein the plurality of circumferentially arranged expandable stent cells are arch-shaped.

11. A method comprising:
    delivering a prosthetic mitral valve to a native mitral valve annulus via a catheter, the prosthetic mitral valve having a self-expanding stent including (a) a proximal atrial section and a distal body section, (b) a prosthetic valve assembly disposed within the body section of the stent, and (c) a cloth member positioned on an exterior surface of the atrial section of the stent, the atrial section of the stent including a first tissue anchor connected to, and flaring radially outward from, a first end of the body section, the first tissue anchor including a plurality of circumferentially arranged expandable stent cells adapted to anchor to a first tissue area on an atrial side of a native mitral valve annulus, the body section of the stent including a plurality of second tissue anchors extending therefrom adapted to anchor to a second tissue area disposed distally to the first tissue area, the cloth member on the atrial section of the stent being adapted to directly contact surrounding heart structure to provide a seal between the atrial section of the stent and the surrounding heart structure;
    allowing the atrial section of the stent to self-expand so that the first tissue anchor engages the first tissue area; and
    engaging the plurality of second tissue anchors to the second tissue area.

12. The method of claim 11, wherein the prosthetic valve assembly is directly coupled to the body section of the stent.

13. The method of claim 11, wherein the cloth member is formed of a material selected from the group consisting of synthetics, pericardium, and polytetrafluoroethylene.

14. The method of claim 11, wherein the cloth member is also positioned on an exterior surface of the body section of the stent.

15. The method of claim 11, wherein the plurality of second tissue anchors includes a plurality of anchoring sutures, and engaging the plurality of second tissue anchors to the second tissue area includes engaging the plurality of anchoring sutures to a wall of a left ventricle or to one or more papillary muscles.

16. The method of claim 11, wherein the body section of the stent has a shape of a truncated cone.

17. The method of claim 11, wherein one side of the body section is flattened relative to another side of the body section, the method including positioning the flattened side of the body section facing a left ventricular outflow tract.

18. The method of claim 11, wherein the plurality of second tissue anchors are attached to a second end of the body section opposite the first end.

* * * * *